US009425022B2

(12) United States Patent
Ogawa et al.

(10) Patent No.: US 9,425,022 B2
(45) Date of Patent: Aug. 23, 2016

(54) MONOCHROMATOR AND CHARGED PARTICLE APPARATUS INCLUDING THE SAME

(71) Applicant: Korea Research Institute of Standards and Science, Daejeon (KR)

(72) Inventors: Takashi Ogawa, Daejeon (KR); Bok Lae Cho, Daejeon (KR); Sang Jung Ahn, Daejeon (KR); In Yong Park, Daejeon (KR); Cheolsu Han, Suwon-si (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 0 days.

(21) Appl. No.: 14/696,569

(22) Filed: Apr. 27, 2015

(65) Prior Publication Data
US 2015/0371811 A1    Dec. 24, 2015

(30) Foreign Application Priority Data

Jun. 20, 2014    (KR) .......................... 10-2014-0075947

(51) Int. Cl.
*H01J 37/05*    (2006.01)
*H01J 49/44*    (2006.01)
(Continued)

(52) U.S. Cl.
CPC ............ *H01J 37/05* (2013.01); *G01N 23/2251* (2013.01); *H01J 37/12* (2013.01);
(Continued)

(58) Field of Classification Search
CPC ............ H01J 37/05; H01J 37/12; H01J 49/44; H01J 49/48; H01J 2237/24485; H01J 2237/05; H01J 2237/053; H01J 2237/057; G01N 23/2251

USPC ........................................................ 250/305
See application file for complete search history.

(56) References Cited

U.S. PATENT DOCUMENTS 6,452,169 B1    9/2002  Mook
6,580,073 B2    6/2003  Plies et al.
(Continued)

FOREIGN PATENT DOCUMENTS

EP    1220292 B1    4/2008

OTHER PUBLICATIONS

Henstra, A. et al, Versatile monochromator module for XHR SEM, Microscopy and Microanalysis, vol. 15, Issue Suppl. 2, Jul. 2009, pp. 168-169.
(Continued)

*Primary Examiner* — Jack Berman
(74) *Attorney, Agent, or Firm* — Perkins IP Law Group LLC; Jefferson Perkins

(57) ABSTRACT

Disclosed herein are a monochromator and a charged particle beam apparatus including the same. The monochromator may include a first electrostatic lens configured to have a charged particle beam discharged by an emitter incident on the first electrostatic lens, refract a ray of the charged particle beam, and include a plurality of electrodes and a second electrostatic lens spaced apart from the first electrostatic lens at a specific interval and configured to have a central axis disposed identically with a central axis of the first electrostatic lens, have the charged particle beam output by the first electrostatic lens incident on the second electrostatic lens, refract the ray of the charged particle beam, and comprise a plurality of electrodes. Accordingly, there is an advantage in that a charged particle beam can have an excellent profile even after passing through the monochromator.

20 Claims, 22 Drawing Sheets

(51) Int. Cl.
*H01J 37/12* (2006.01)
*G01N 23/225* (2006.01)
*H01J 37/21* (2006.01)

(52) U.S. Cl.
CPC ............. *H01J 37/21* (2013.01); *H01J 49/44* (2013.01); *H01J 2237/057* (2013.01); *H01J 2237/1516* (2013.01); *H01J 2237/2448* (2013.01); *H01J 2237/24485* (2013.01)

(56) References Cited

U.S. PATENT DOCUMENTS

| | | | |
|---|---|---|---|
| 7,034,315 B2 * | 4/2006 | Henstra | H01J 37/05 250/305 |
| 7,745,783 B2 | 6/2010 | Uhlemann | |
| 7,999,225 B2 * | 8/2011 | Henstra | H01J 3/027 250/305 |
| 8,461,525 B2 | 6/2013 | Henstra | |
| 8,710,452 B2 | 4/2014 | Henstra | |
| 8,853,616 B2 | 10/2014 | Mukai | |
| 9,111,715 B2 * | 8/2015 | Parker | H01J 37/05 |
| 2008/0290273 A1 | 11/2008 | Uhlemann | |
| 2012/0112090 A1 * | 5/2012 | Henstra | H01J 37/05 250/396 R |
| 2012/0223244 A1 * | 9/2012 | Welkie | H01J 37/12 250/396 ML |
| 2013/0248699 A1 | 9/2013 | Mukai | |

OTHER PUBLICATIONS

Mook, H.W. et al, Construction and Characterization of the fringe field monochromator for a field emission gun, Ultramicroscopy 81(2000) 129-139.

Mukai, M. et al, Monochromator for a 200 kV analytical electron microscope, Microscopy and Microanalysis vol. 12, Issue Suppl. 2, Aug. 2006, pp. 1206-1207.

Plies, E. et al., The Wien filter : History, fundamentals and modern applications, Nuclear Instruments and Methods in Physics Research A, 645 (2011) 7-11.

Uhlemann, Stephen et al., Experimental Set-Up of a Purely Electrostatic Monochromator for High Resolution and Analytical Purposes of a 200kV TEM, Microsc. Microanal. 8, Suppl. 2 (2002) 584CD-585CD.

* cited by examiner

Fig. 16
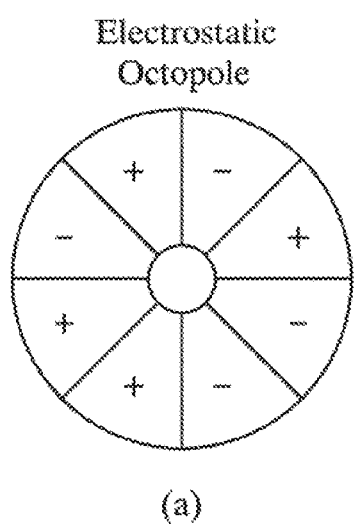
(a) Electrostatic Octopole
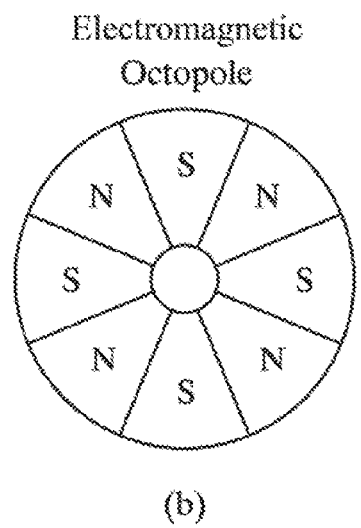
(b) Electromagnetic Octopole

MONOCHROMATOR AND CHARGED PARTICLE APPARATUS INCLUDING THE SAME

CROSS REFERENCE TO RELATED APPLICATION

The present application claims the benefit of Korean Patent Application No. 10-2014-0075947 filed in the Korean Intellectual Property Office on Jun. 20, 2014, the entire contents of which are incorporated herein by reference.

BACKGROUND OF THE INVENTION

1. Technical Field

The present invention relates to a monochromator and a charged particle beam apparatus including the same and, more particularly, to a monochromator (MC) for matching optical axes with a low cost and a charged particle beam apparatus including the same.

2. Description of the Related Art

A monochromator is an apparatus for supplying light of a narrow wavelength range and is optics/monochrome spectrometer for extracting desired monochromatic light by performing spectroscopy on white light through a combination of a lens and a slit. Such a monochromator is used optics in a charged particle beam apparatus or used as an energy analyzer. An example of a conventional monochromator is described below.

In relation to a Mollenstedt energy analyzer MA, FIG. 1 is a side cross-sectional view and plan view illustrating the Mollenstedt energy analyzer MA. As illustrated in FIG. 1, the Mollenstedt energy analyzer MA is a charged particle energy analyzer using the off-axis chromatic aberration of a cylindrical lens CylL. The cylindrical lens is a charged particle lens in which a rectangular opening is formed at the center of three electrodes 11, a high voltage is applied to the center electrode, and two electrodes on both sides are used as ground voltages. An insulating material 12 is provided between the three electrodes 11. Energy of electrons is decelerated almost close to 0 near the center electrode, a component that passes through the outside of the optical axis of the cylindrical lens is selected, and energy of charged particles is analyzed using an energy dispersion generated by the chromatic aberration of the lens axis. Such an energy analyzer is named the Mollenstedt energy analyzer MA by taking the inventor's name.

In relation to a monochromator using an electrostatic lens of FEI Co., Ltd., FIG. 2 is a diagram illustrating a monochromator of FEI Co., Ltd. As illustrated in FIG. 2, the monochromator of the FEI Co., Ltd. is a monochromator MC for selecting the off-axis component of an electron source by an aperture, passing the selected component through the outside of an electrostatic lens, and performing monochrome (i.e., enlarging or reducing energy) on the component by performing spectroscopy on the energy. The monochromator may be used in a charged particle beam apparatus, such as a scanning electron microscope (SEM). Such a monochromator can improve resolution of an image by reducing the influence of a chromatic aberration (Patent document 0001).

In relation to monochromators of Delft University of Technology, JEOL Co., Ltd., and Tubingen University, FIGS. 3 to 5 are diagrams illustrating the monochromators of Delft University of Technology, JEOL Co., Ltd., and Tubingen University. As illustrated in FIGS. 3 to 5, a Wien Filter type monochromator MC is mounted on the electron gun of a transmission electron microscope (TEM) or scanning transmission electron microscope (STEM), energy is subject to spectroscopy, and monochrome may be performed on the energy (i.e., an energy distribution may be reduced) (Patent document 0002 to 0004).

In relation to a monochromator of CEOS Co., Ltd., FIG. 6 is a diagram illustrating a monochromator of CEOS Co., Ltd. As illustrated in FIG. 6, a 4-stage electrostatic deflector is mounted on the electron gun of a transmission electron microscope (TEM) or scanning transmission electron microscope (STEM), energy is subject to spectroscopy, monochrome may be performed on the energy (i.e., an energy distribution may be reduced) (Patent document 0005). In accordance with the monochromator of CEOS Co., Ltd., there is an advantage in that resolution of an image is improved in an energy region of 60 keV or less that is lower than common 200 keV because the influence of a chromatic aberration is reduced. Furthermore, energy resolution in an electron energy loss spectroscopy (EELS) on the lower side can be improved.

3. Cited References (Patent Document 001) Henstra, Charged Particle source with integrated energy filter, US8461525B2
(Patent Document 0002) Hindrik Willem Mook, Wien filter, U.S. Pat. No. 6,452,169 B1
(Patent Document 0003) Masaki Mukai, Method of adjusting transmission electron microscope, US2013/0248699 A1
(Patent Document 0004) Erich Piles, Monochromator for charged particles, EP1220292B1
(Patent Document 0005) Uhlemann, Monochromator and radiation source with monochromator, US2008/0290273A1

SUMMARY OF THE INVENTION

However, the aforementioned conventional monochromators are problematic in that they are complicated in structures and very expensive and they require a high level of precision in fabrication and a large number of power sources.

In particular, the monochromator MC of FEI Co., Ltd. illustrated in FIG. 4 has the simplest structure, but is problematic in that an off-axis aberration, such as coma and astigmatism, remains in order for a charged particle beam to pass through the outside of the axis of a lens and the profile of the charged particle beam is adversely affected at the back. Furthermore, there is a problem in that energy spread of the original electron beam is increased and an emission current becomes unstable if a component in the axis of an electron source is to be used. Furthermore, energy resolution (i.e., narrow energy spread) higher than 10 meV is required for a sample and the phonon spectroscopy of absorbed gas molecules on a surface of the sample.

Accordingly, the present invention has been made keeping in mind the above problems occurring in the prior art.

An object of the present invention is to provide a monochromator in which a two-stage cylindrical lens CylL is offset from an optical axis and disposed, a slit is disposed between first-stage and second-stage cylindrical lenses CylL, the first-stage cylindrical lens CylL deflects a charged particle beam and disperses energy, the slit selects the energy, the second-stage cylindrical lens CylL deflects the charged particle beam in an opposite direction so that the optical axis of the deflected charged particle beam is matched with the original optical axis, and a charged particle beam apparatus using the monochromator. The monochromator does not have a secondary aberration and primary energy dispersion generated in the first-stage cylindrical lens and can obtain an excellent profile of a charged particle beam even after the charged particle passes through the monochromator. In other words, there is an advantage in that a charged particle beam in the central part of an emitter can be used.

BRIEF DESCRIPTION OF THE DRAWINGS

The following drawings attached to this specification illustrate exemplary embodiments of the present invention and function to facilitate further understanding of the technical spirit of the present invention along with the detailed description of the invention. Accordingly, the present invention should not be construed as being limited to only matters illustrated in the drawings.

FIGS. 14, 15, and 16 are diagrams illustrating a multipole in accordance with another embodiment of the present invention;

DESCRIPTION OF REFERENCE NUMERALS OF PRINCIPAL ELEMENTS IN THE DRAWINGS

Figure 1:
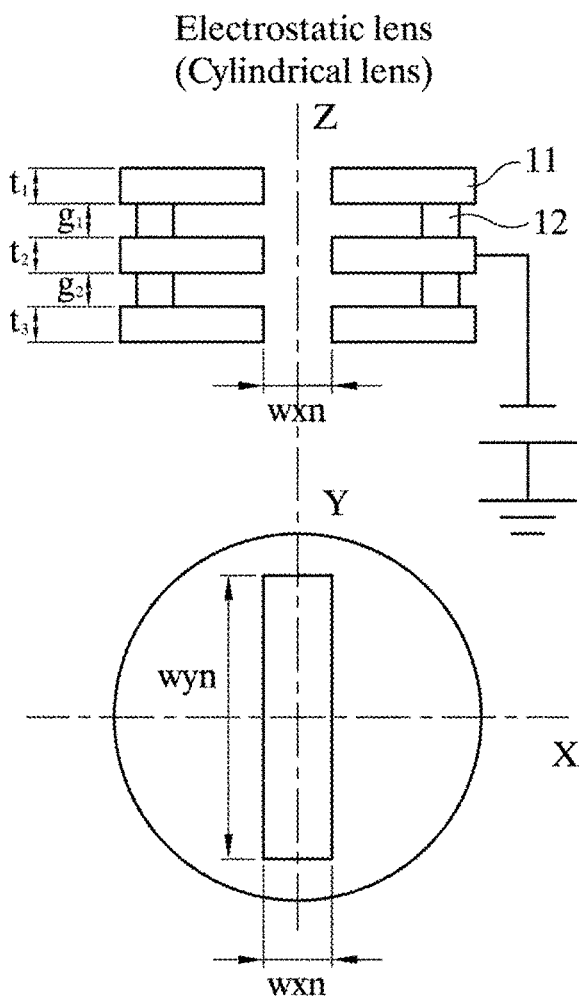
FIG. 1 is a side cross-sectional view and plan view illustrating a cylindrical lens CylL.
Figure 2:
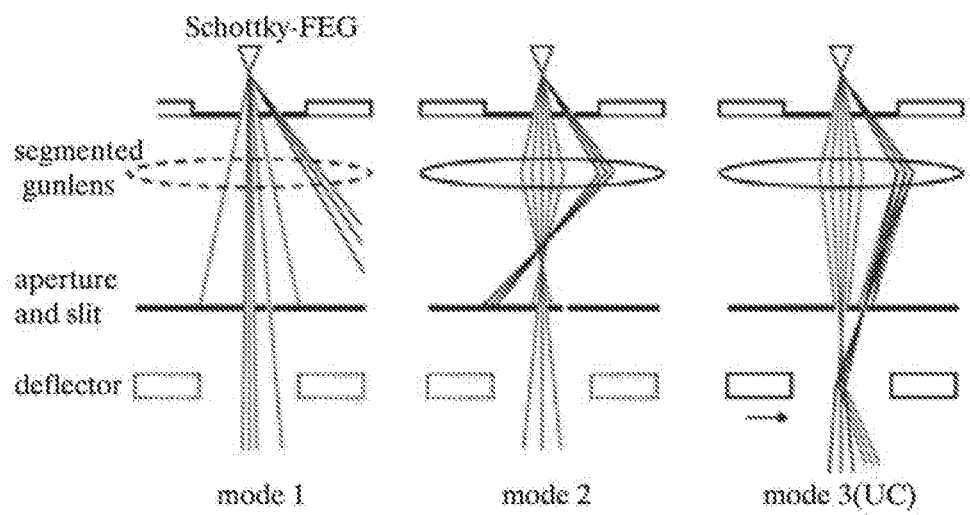
FIG. 2 is a diagram illustrating a monochromator of FEI Co., Ltd.
Figure 3:
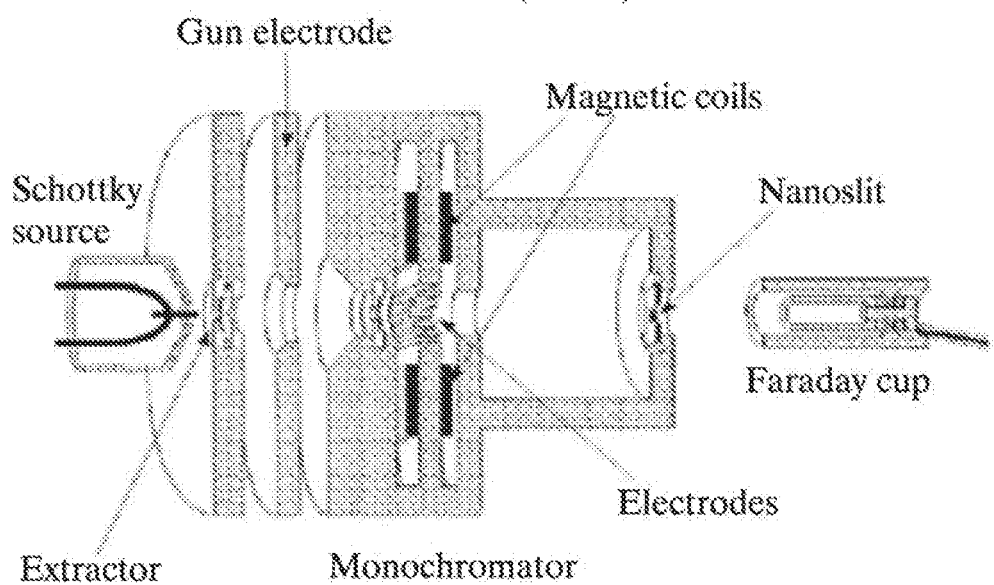
FIGS. 3 to 5 are diagrams illustrating monochromators of Delft University of Technology, JEOL Co., Ltd., and Tubingen University.
Figure 4:
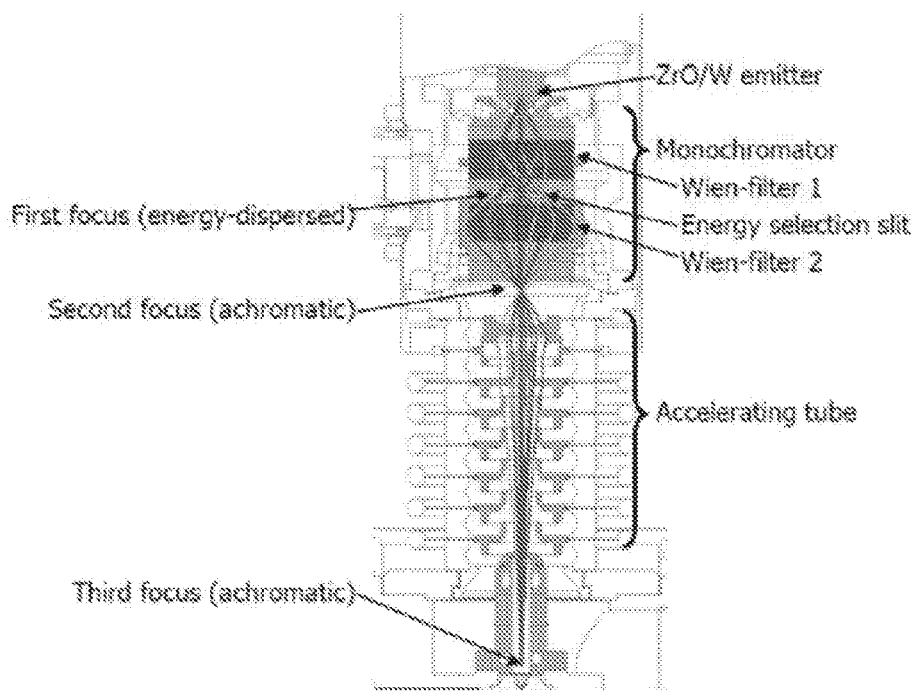
Figure 5:
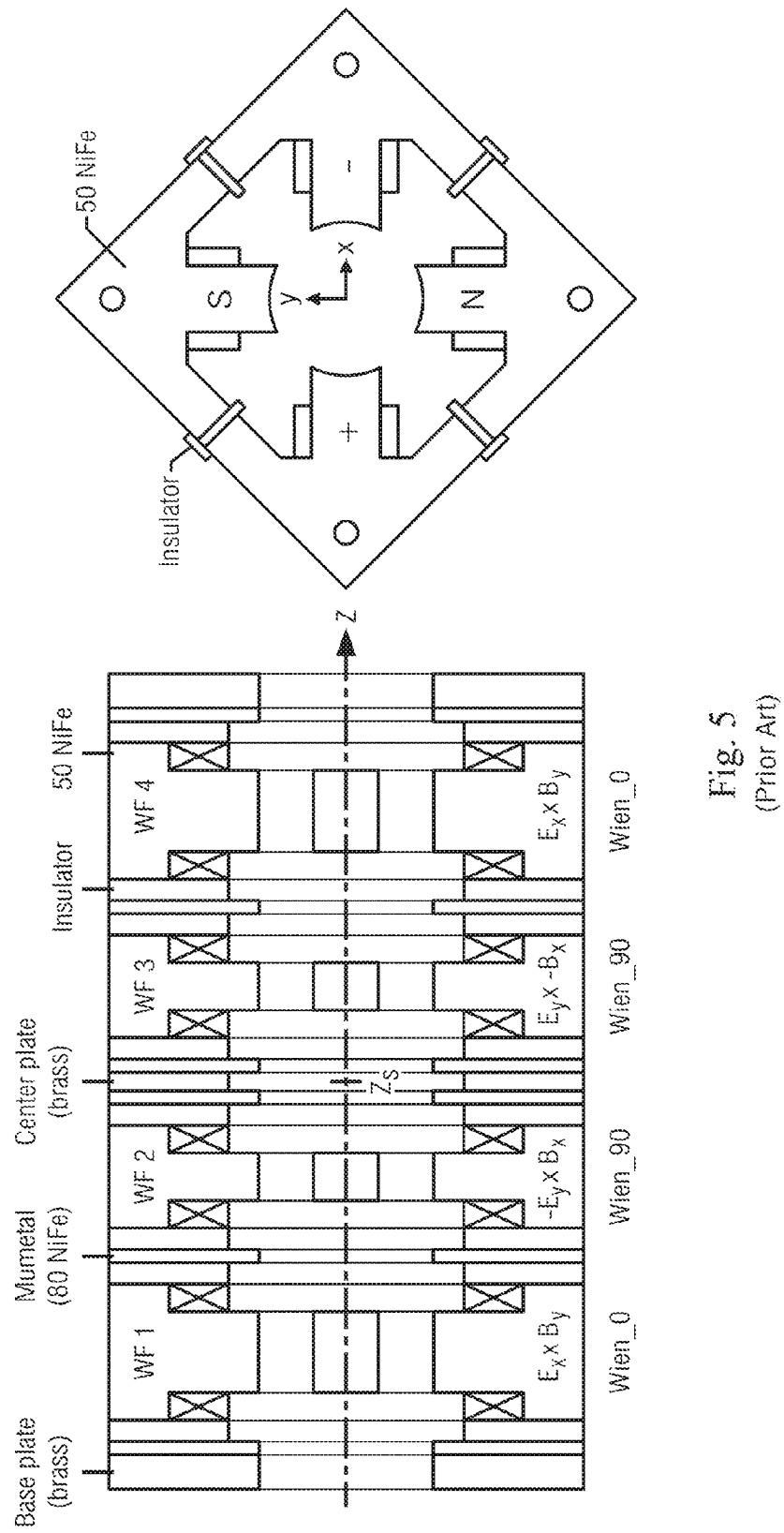
Figure 6:
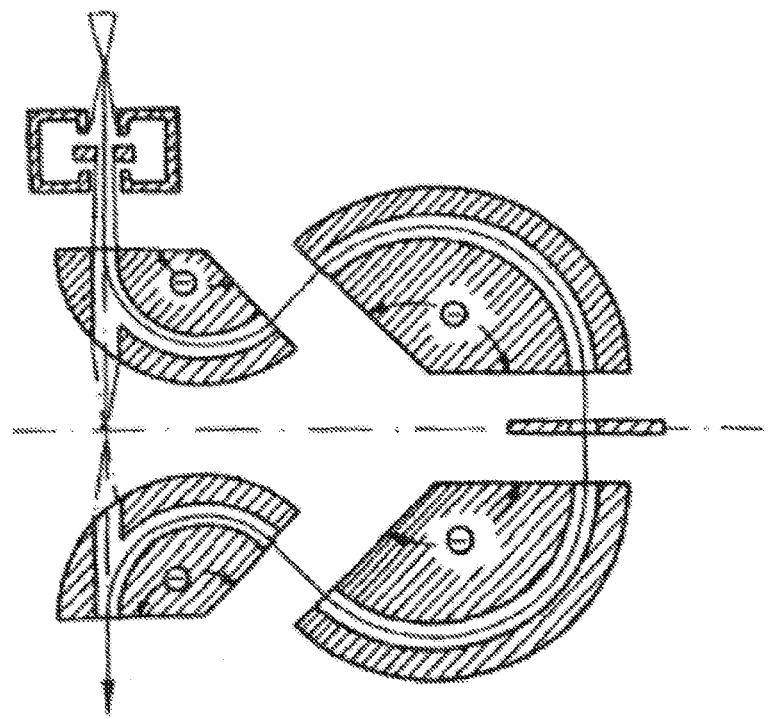
FIG. 6 is a diagram illustrating a monochromator of CEOS Co., Ltd.

| 1: emitter | 4: optics |
|---|---|
| 5: detector | 6: sample |
| 7: vacuum chamber | 8: vacuum pump |
| 9: screen | 11: electrode |
| 12: insulating material | |
| 20: electron beam loss spectroscopy (EELS) | |
| 31: yoke | 32: coil |
| 33: gap | 34: pole piece |
| 40: illumination optics | 42: projection optics |
| 50: accelerator | 60: stage |
| X: charged particle beam | Xd: offset |
| Xk: another axial ray | Xα, Xγ: para-axial ray |
| Yβ, Yδ: para-axial ray | MC: monochromator |
| TL1: first transfer lens | TL2: second transfer lens |
| CylL1: first cylindrical lens | |

| CylL2: second cylindrical lens | |
|---|---|
| OL: object lens | CL: focusing lens |

DETAILED DESCRIPTION

Hereinafter, some exemplary embodiments of the present invention are described in detail with reference to the accompanying drawings in order for those skilled in the art to be able to readily practice them. In describing an operational principle relating to the embodiments of the present invention, however, when a detailed description of relevant functions or constructions is deemed to make the subject matter of the present invention unnecessarily obscure, the detailed description will be omitted.

Furthermore, the same reference numerals designate elements having similar functions and operations throughout the drawings. Throughout the specification, when it is described that one specific element is connected to the other element, the specific one element may be directly connected to the other element or indirectly connected to the other element through a third element. Furthermore, when it is described that specific element includes another element, it means that the specific element does not exclude another element, but may include other elements, unless otherwise described.

Monochromator

In relation to a monochromator in accordance with an embodiment of the present invention, the configuration and functions of the monochromator in accordance with an embodiment of the present invention are described below.

In relation to a cylindrical lens used in a monochromator in accordance with an embodiment of the present invention, FIG. 1 is a side cross-sectional view and plan view illustrating a cylindrical lens CylL. As illustrated in FIG. 1, the direction in which a charged particle beam travels is defined as a Z direction, an X direction is defined as the short side of the rectangular opening of the cylindrical lens, and a Y direction is defined as the long side of the rectangular opening of the cylindrical lens. The cylindrical lens has a strong lens action in the X direction and has a weak lens action in the Y direction.

A two-stage cylindrical lens CylL is used in the monochromator in accordance with an embodiment of the present invention. The central axis of the two-stage cylindrical lens CylL is offset from an optical axis in which the optical equipment (e.g., emitter (or electron source), transfer lens TL, and object lens OL of the charged particle beam apparatus are placed at a specific interval in the X direction and disposed. The size of the offset is denoted by an Xd.

Figure 7:
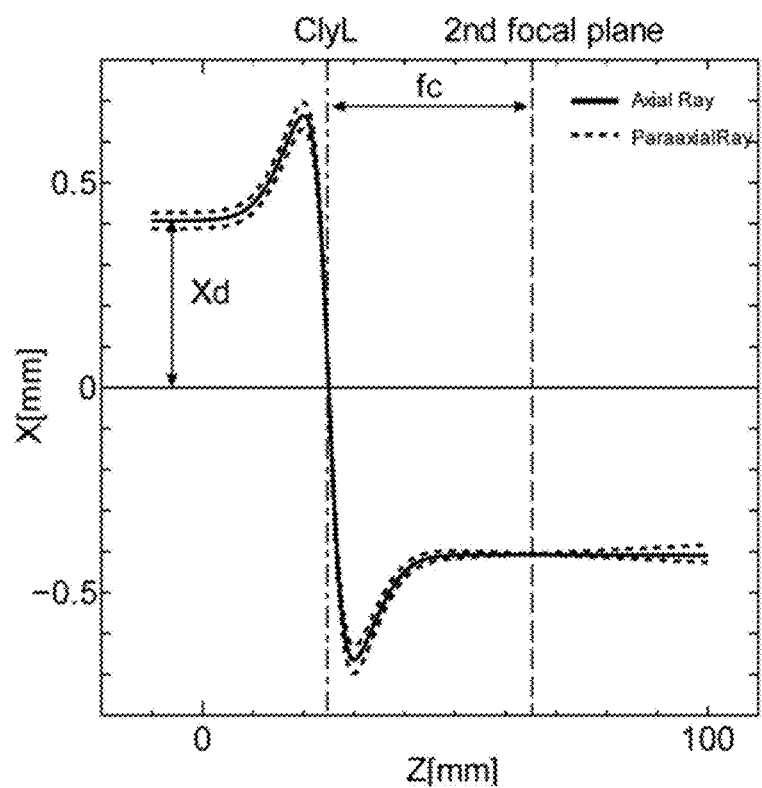
FIG. 7 is a Z-X axis displacement graph regarding the ray of a charged particle beam in accordance with an embodiment of the present invention.

FIG. 7 is a Z-X axis displacement graph of the ray of a charged particle beam in accordance with an embodiment of the present invention. As illustrated in FIG. 7, the charged particle beam is output from the emitter in the optical axis having the offset of Xd from the center of the cylindrical lenses CylL 1&2, and the axial ray of the charged particle beam is so that it is symmetrical on the basis of the X axis while passing through the cylindrical lens CylL.

The cylindrical lens may include a lens having a higher refractive index than a common lens. In this case, a lens in which the number of faces on which an image of a charged particle beam is focused is one or two (i.e., a $2^{nd}$ focus) may be used as the cylindrical lens. A lens condition in this region is spaced apart from the center axis of the cylindrical lens by the offset. The off-axis ray of the charged particle beam that is incident in parallel is converged on the central axis once (i.e., focused) and output in parallel to the central axis. The distance between the central axis and the exit orbit becomes the same condition as the offset when the charged particle beam is incident.

If an off-axis ray that is incident in parallel and output in parallel is defined as an axial ray, a ray emitted at a small angle with respect to the axial ray may be defined as a para-axial ray. It was found that such a para-axial ray is converged on the center of the first and the second cylindrical lenses and the axial ray once in addition to the center of the first and the second cylindrical lenses through the calculation of the ray of the charged particle beam of FIG. 7.

In FIG. 7, fc, that is, the second focal distance of the cylindrical lens may be defined as the distance from the location where the para-axial ray incident in parallel to the axial ray is converged on the axial ray twice to the center of the cylindrical lens. In the monochromator in accordance with an embodiment of the present invention, if such cylindrical lenses are fabricated so that they are symmetrical to each other left and right in the central axis of the monochromator (i.e., the center of the first and the second cylindrical lenses CylL 1&2), the distance between a focus before the para-axial ray emitted from the emitter in a specific angle to the axial ray becomes parallel to the axial ray after passing through the two-stage cylindrical lens and the center of the two-stage cylindrical lens is the same as the second focal distance "fc".

Figure 8:
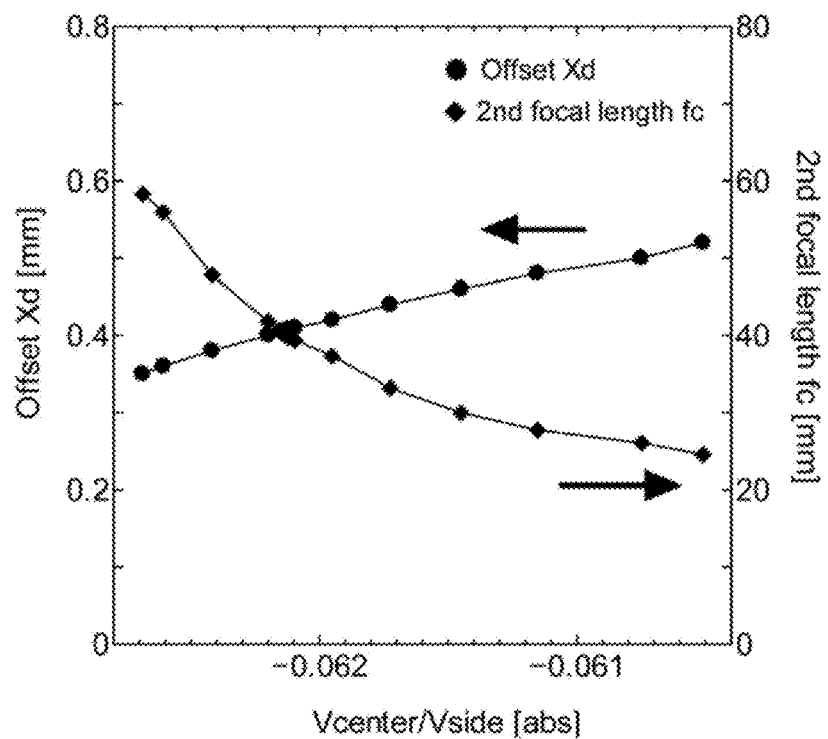
FIG. 8 is a graph of an offset condition according to a ratio of voltages applied to electrodes in according with an embodiment of the present invention.

Such a para-axial ray may be described by the second focal distance "fc" as in a common lens system. FIG. 8 is a graph of the offset condition according to a ratio of voltages Vcenter/Vside applied to the center electrode and the electrodes on both sides in according with an embodiment of the present invention. In FIG. 8, the offset Xd and the second focal distance "fc" are illustrated with respect to the voltage Vcenter applied to the center electrode of the cylindrical lens through the simulations of optics. In FIG. 8, an X axis is a ratio of the voltages applied to the electrodes derived by dividing the voltage Vcenter applied to the center of the electrodes of the cylindrical lens by the voltage Vside of the electrodes on both sides. The voltages Vcenter and Vside are numerical values when the potential of the emitter (i.e., electron source) is set to 0. The voltage Vcenter may be the same as an extraction voltage and may be set to 4 kV in an embodiment of the present invention. A negative voltage Vcenter means that a voltage lower than the potential of the emitter is applied to the center electrode.

In relation to the relation between the offset Xd and the ratio of the voltages Vcenter/Vside applied to the electrodes 11, the relation is determined by a shape of the cylindrical lens. More specifically, the relation is determined by the thicknesses t1, t2, and t3 of the respective electrodes 11 of FIG. 1, the intervals g1 and g2 of the respective electrodes 11, and the widths wx1, wx2, wx3, wy1, wy2, and wy3 of an opening in X and Y directions. In an embodiment of the present invention, the graph of FIG. 8 was obtained by performing calculation assuming that t1=t2=t3=10 mm, g1=g2=10 mm, wx1=wx2=wx3=10 mm, and wy1=wy2=wy3=100 mm.

Figure 9:
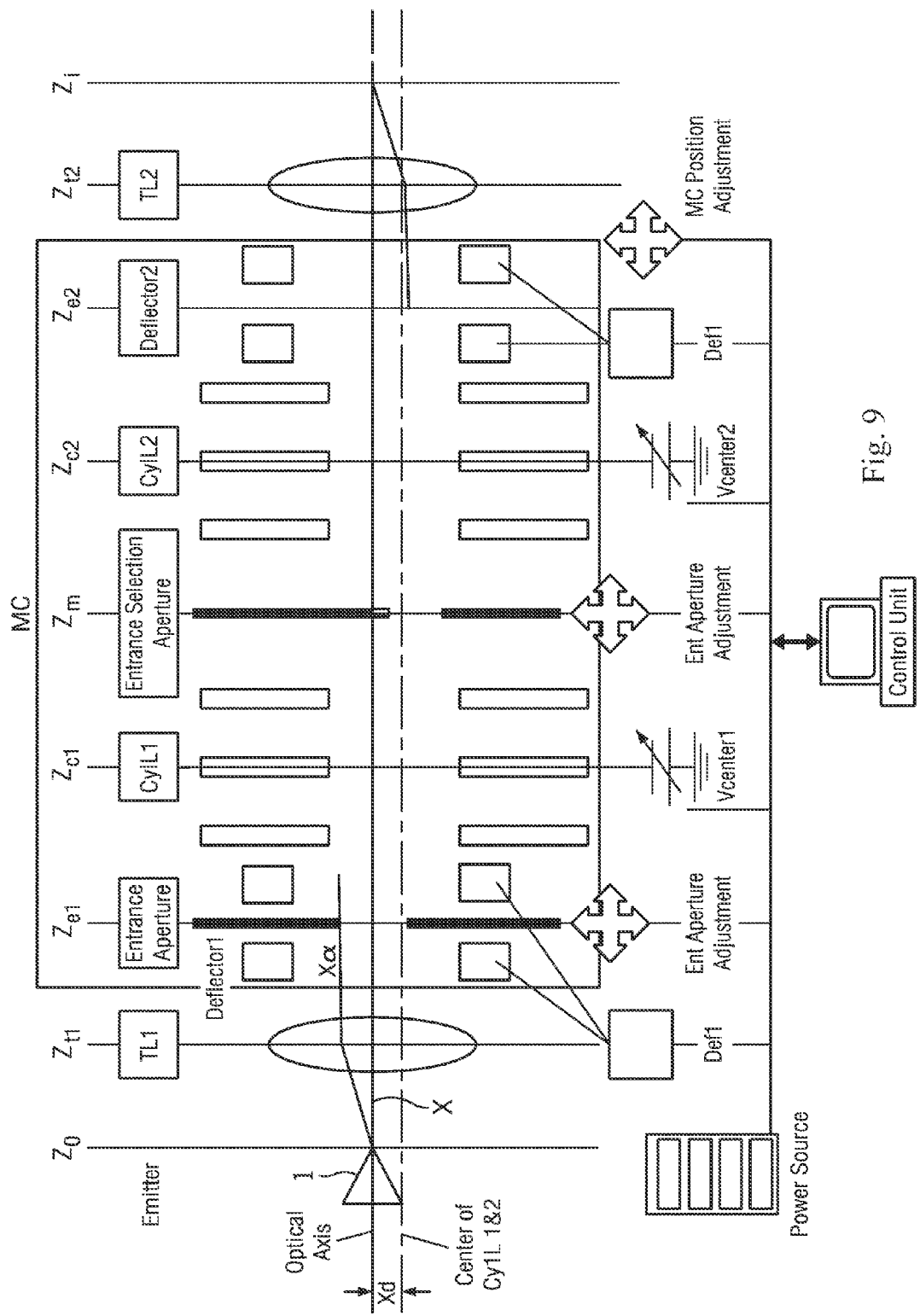
FIGS. 9 and 10 are diagrams illustrating a monochromator in accordance with an embodiment of the present invention.

FIG. 9 is a diagram illustrating a monochromator in accordance with an embodiment of the present invention. As illustrated in FIG. 9, in the monochromator MC in accordance with an embodiment of the present invention, the two-stage cylindrical lens CylL1, CylL2 may be disposed in the Z direction so that they are spaced apart from each other at an interval 2fc that is twice fc in FIG. 7. In an embodiment of the present invention, relation data (FIG. 8) between the previously calculated offset Xd and a ratio of the voltages Vcenter/Vside applied to the electrodes 11 may be stored in a control unit (e.g., a control PC). The center of the two-stage cylindrical lens CylL1, CylL2 may be offset by the offset Xd in the optical axis, that is, the optical axis in which the charged particle beam X is output from the emitter based on the relation data. Almost the same value as the voltage Vcenter may be used as the voltages Vcenter1 and Vcenter2 at the center electrodes of the cylindrical lens. Theoretically, the two center electrode voltages Vcenter1 and Vcenter2 of the two-stage cylindrical lens need to be identical with the voltage Vcenter. Practically, the electrodes of the cylindrical lenses CylL1 and CylL2 may need to have two independent power sources because fine adjustment is required by the degree of mechanical assembly. Furthermore, a position adjustment unit for the two-stage cylindrical lens in the X direction may be provided outside a vacuum chamber.

Under the relation condition between the offset Xd and the ratio of the voltages Vcenter/Vside applied to the electrodes 11 in FIG. 9, the charged particle beam X in the optical axis is deflected in a direction opposite the offset Xd in the first cylindrical lens CylL1, that is, a first-stage cylindrical lens, output with the same offset in parallel to the optical axis, and returned back by the second cylindrical lens CylL2, that is, a second-stage cylindrical lens to which the same voltage is applied, thus drawing an orbit at the location identical with the optical axis. That is, a thick solid line in FIG. 9 means the axial ray of the charged particle beam X, and a chain dashed line means the optical axis and the center of the first and the second cylindrical lenses CylL 1&2. As illustrated in FIG. 9, the axial ray of the charged particle beam X is refracted in a direction opposite the center of the first and the second cylindrical lenses CylL 1&2 by the two-stage cylindrical lens, and returns back to the optical axis.

Figure 10:
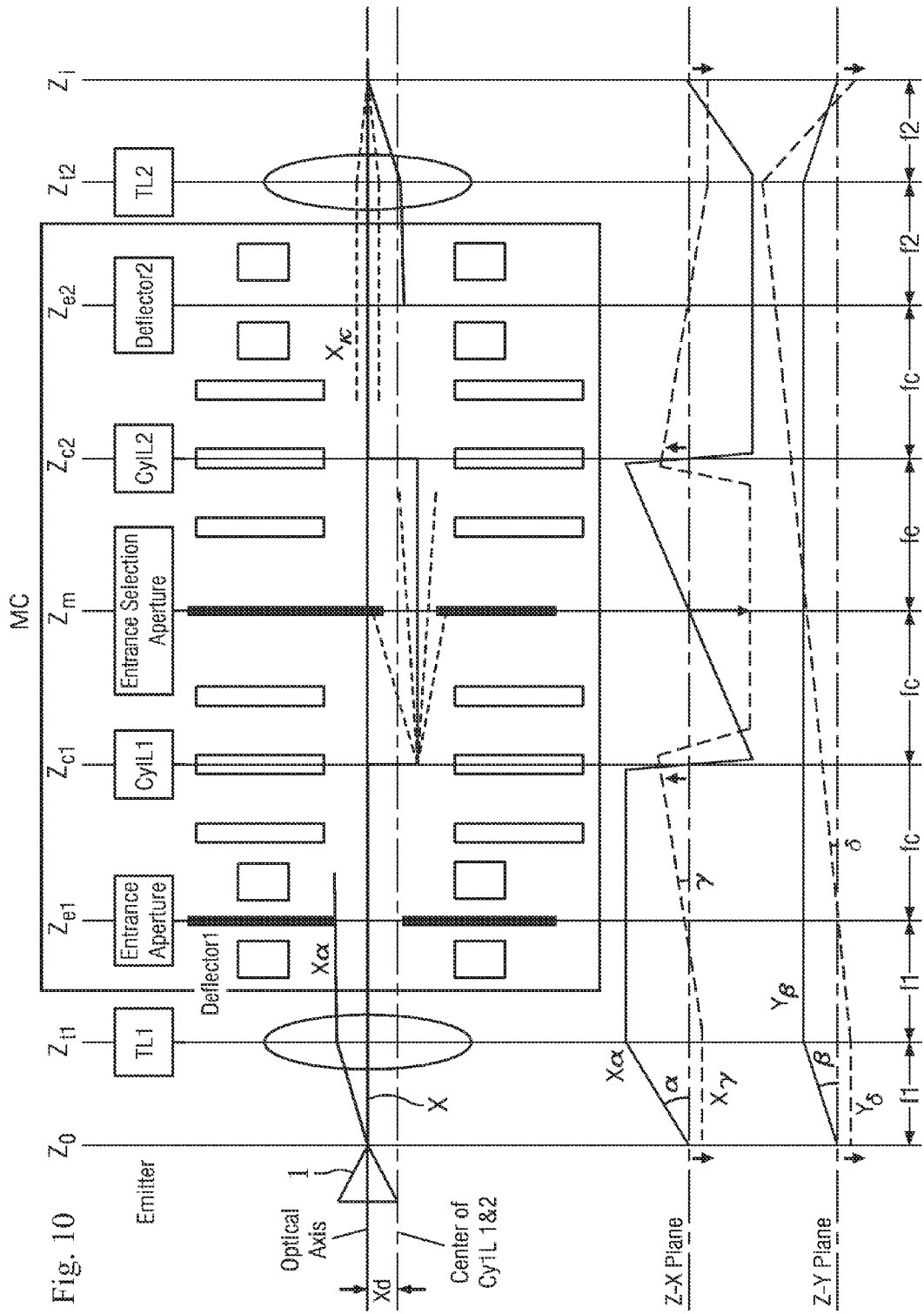

FIG. 10 is a diagram illustrating a monochromator in accordance with an embodiment of the present invention. In a graph illustrating a Z-X plane and a Z-Y plane illustrated on the lower side of FIG. 10, the axial ray that is refracted by the two-stage cylindrical lens and travels is indicated by a straight line so that visually improved access is obtained with respect to the relation between the para-axial ray and the axial ray.

In the Z-X plane on the lower side of FIG. 10, $X\alpha$ (indicated by a solid line) means a para-axial ray that is incident in the state in which it has been deviated from the axial ray at an angle of $\alpha$. In the Z-X plane, $X\gamma$ (indicated by a dotted line) means a para-axial ray that is incident in parallel to the axial ray. The para-axial ray $X\gamma$ of the charged particle beam X discharged by the emitter 1 is deviated from the axial ray by an angle $\gamma$ in the X axis direction while passing through the first transfer lens TL1. The para-axial ray $X\gamma$ is deviated from the axial ray at an angle of $-\gamma$ in the X axis direction while passing through the first and the second cylindrical lenses CylL1 and CylL2. The para-axial ray $X\gamma$ is output in parallel to the axial ray in the same direction in which the para-axial ray $X\gamma$ has passed through a second transfer lens TL2.

In the Z-X plane on the lower side of FIG. 10, the para-axial ray $X\alpha$ of the charged particle beam X discharged by the emitter 1 is incident on the first transfer lens TL1 at an angle $\alpha$ with the axial ray in the X axis direction. The para-axial ray $X\alpha$ travels in parallel to the axial ray while passing through the first transfer lens TL1. The para-axial ray $X\alpha$ become symmetrical to the axial ray in the X axis while passing through the first and the second cylindrical lenses CylL1 and CylL2, and travel in parallel to the axial ray. The para-axial ray $X\alpha$ is output in the same direction in which it has been incident while passing through the second transfer lens TL2 after passing through the first and the second cylindrical lenses CylL1 and CylL2.

In the Z-Y plane on the lower side of FIG. 10, Yβ (indicated by a solid line) means a para-axial ray incident in the state in which it has been deviated from the axial ray at an angle of β in the Y axis direction. In the Z-Y plane, Yδ (indicated by a dotted line) means a para-axial ray incident in parallel to the axial ray. From FIG. 10, it may be seen that the para-axial ray Yδ and the para-axial ray Yβ do not have a change of orbits in the Y axis direction and are not focused.

As illustrated on the lower side of FIG. 10, the distance between the emitter 1 and the first transfer lens TL1 and between the first transfer lens TL1 and the entrance aperture may be defined as f1, that is, the focal distance of the first transfer lens TL1. The distance between the entrance aperture in which a first deflector Deflector1 has been installed and the first cylindrical lens CylL1, between the first cylindrical lens CylL1 and a energy selection aperture, between the energy selection aperture and the second cylindrical lens CylL2, and between the second cylindrical lens CylL2 and a second deflector Deflector2 may be defined as fc, that is, the second focal distance of the cylindrical lens which may be seen in FIG. 7. Furthermore, the distance between the second deflector Deflector2 and the second transfer lens TL2 and between the second transfer lens TL2 and the location Zi may be defined as f2, that is, the focal distance of the second transfer lens.

As illustrated in FIG. 10, the para-axial ray Xα incident to the cylindrical lens in parallel to the axial ray at a location Ze1, that is, the distance at the center of the first and the second cylindrical lenses is fc in front of the first cylindrical lens CylL1, is focused on the axial ray near the central part of the first cylindrical lens CylL1. Thereafter, the para-axial ray Xα is output by the first cylindrical lens CylL1 and then focused on the axial ray at a location Zm whose distance is fc at the center of each of the first and the second cylindrical lenses CylL1 and CylL2 in the middle of the cylindrical lenses. In the second cylindrical lens CylL2, the para-axial ray Xα takes an asymmetric ray, focused on the axial ray within the second cylindrical lens CylL2, and then output in parallel to the axial ray at a location Ze2 whose distance is fc at the center of the cylindrical lenses toward the rear of the second cylindrical lens CylL2. In accordance with an embodiment of the present invention, the ray of the charged particle beam X is focused on the axial ray three times in the X direction.

The para-axial ray Xγ that travels at the angle γ in the axial ray at the location Ze1 whose distance is fc at the center of the cylindrical lens in front of the first cylindrical lens CylL1 is focused on the axial ray within the first cylindrical lens CylL1, and travels in parallel to the axial ray at Zm, that is, at the middle location of the first and the second cylindrical lenses CylL1 and CylL2. Thereafter, the para-axial ray Xγ has a symmetric ray in the second cylindrical lens CylL2, focused on the axial ray within the second cylindrical lens CylL2, and then focused on the axial ray at the location Ze2, that is, fc whose distance is fc at the center of the cylindrical lens in the rear of the second cylindrical lens CylL2.

As illustrated in FIG. 10, the configuration of the monochromator MC in accordance with an embodiment of the present invention may be defined as 4$f$ optics because it has a relation that is four times the focal distance fc. An image of the same phase at the location Ze1 in the X direction is equally formed at the location Ze2. In an embodiment of the present invention, the optics may be configured by setting the disposition of the first and the second cylindrical lenses CylL1 and CylL2, the amount of the offset, and the center voltages Vcenter1 and Vcenter2 depending on the relation condition between the calculated offset Xd of FIG. 9 and the ratio of the voltages Vcenter/Vside applied to the electrodes 11.

As illustrated in FIG. 10, in the monochromator MC in accordance with an embodiment of the present invention, the entrance aperture that limits an angle on which the charged particle beam is incident at the location Ze1 whose distance is fc at the center of the lenses in front of the first cylindrical lens CylL1. As illustrated in FIG. 10, there is an advantage in that there is no influence because the para-axial ray Xγ is focused on the axial ray at the location Ze1 and an incident angle of the para-axial ray Xα can be determined. Furthermore, the monochromator MC in accordance with an embodiment of the present invention may include the fine adjustment unit having a function for controlling the location of the entrance aperture outside the vacuum apparatus.

As illustrated in FIG. 10, in the monochromator MC in accordance with an embodiment of the present invention, the energy selection aperture for selecting energy of an incident charged particle beam at the location Zm, that is, the center of the first and the second cylindrical lenses CylL1 and CylL2. As illustrated in FIG. 10, there is an advantage in that energy can be efficiently selected from the energy of the charged particle beam at the location Zm because an energy dispersion in which different axial rays pass through different locations. In FIG. 10, a different axial ray of the charged particle beam is indicated by Xk. A ray that is not limited is output by the energy selection aperture in parallel to the axial ray at the location Ze2 in the rear of the second cylindrical lens CylL2. Furthermore, the monochromator MC in accordance with an embodiment of the present invention may include the fine adjustment unit having a function for controlling the location of the entrance aperture outside the vacuum apparatus.

As illustrated in FIG. 10, in the monochromator MC in accordance with an embodiment of the present invention, the first transfer lens TL1 may be placed at the location Zt1, that is, the location of an f1 distance that is ahead of the location Ze1, that is, the location of the entrance aperture. The emitter 1 is placed at the location Zo, that is, the f1 distance in front of the first transfer lens TL1. Accordingly, the ray of the charged particle beam output by the emitter 1 at a specific angle can travel in parallel to the axial ray and the ray of the charged particle beam output by the emitter 1 in parallel to the axial ray can travel in such a way as to properly set the condition of the first transfer lens TL1 by taking into consideration of the energy of the extraction voltage of the emitter 1. Accordingly, the charged particle beams may be focused on the axial ray at the location Ze1. Such a condition is the same as the focal distance f1 of the first transfer lens TL1. Furthermore, the condition may determine the amount of current of the charged particle beam that is incident depending on the diameter of the entrance aperture at the location Ze1. The para-axial ray Xγ output by the emitter 1 in parallel to the axial ray is focused on the axial ray at the location Ze1. Accordingly, a more uniform profile of the charged particle beam can be obtained because an electric current is not limited by the location at which the charged particle beam of the emitter 1 is emitted. Furthermore, there is an advantage in that a constant focal distance f1 can be maintained in such a manner that a change of the extraction voltage depending on the size or state of the emitter 1 by offsetting a change of the extraction voltage by changing the first transfer lens TL1.

As illustrated in FIG. 10, in the monochromator MC in accordance with an embodiment of the present invention, the second transfer lens TL2 may be placed at a location Zt2 having a distance of f2 at the back further behind the location Ze2 whose distance from the center of the lens is fc in the rear of the second cylindrical lens CylL2. The condition of the second transfer lens TL2 may be properly set depending on energy applied to the charged particle beam, and the focal distance of the second transfer lens TL2 is defined as f2. The para-axial ray Xα incident on the first cylindrical lens CylL1 in parallel thereto is focused on the axial ray the location Zi behind the second transfer lens TL2 placed at the location Zt2. The para-axial ray Xγ that is output at a specific angle γ with respect to the axial ray at the location Ze1 and focused on the axial ray at the location Ze2 behind the second cylindrical lens CylL2 becomes parallel to the axial ray at the location Zt2, that is, the location of the second transfer lens TL2.

In accordance with the configuration of the optics according to an embodiment of the present invention, an image of the emitter 1 may be formed at the location Zi having a distance of f2 in the rear of the second transfer lens TL2. Since images of the first and the second cylindrical lenses CylL1 and CylL2, that is, the two-stage cylindrical lens in the X direction, are formed equal times at the location Ze1 and the location Ze2, all the magnifications between the location Zo and the location Zi are determined by a ratio f2/f1 of the focal distances of the two transfer lenses TL1 and TL2. If the focal distances of the first transfer lens TL1 and the second transfer lens TL2 are made identical with each other, the magnification becomes 1, and an image having the same magnification as that of the emitter 1 is formed at the location Zi. Furthermore, a para-axial ray Xk that is not limited in the energy selection aperture and that has different energy is output almost in parallel to the axial ray at the location Ze2 behind the second cylindrical lens CylL2 and focused on the axial ray the location Zi, that is, the same location, by the second transfer lens TL2. Accordingly, at such a location Zi, an image of an achromatic light source having the same energy can be obtained.

As illustrated in FIG. 10, in the monochromator MC in accordance with an embodiment of the present invention, the two-stage cylindrical lens CylL1, CylL2 may not almost have a focusing action in the Y direction. The square aperture of the entrance of a cylindrical lens in the Y direction, such as that illustrated in FIG. 1, may be configured to be 10 times greater than an aperture in the X direction so that a focusing action is generated in the X direction, but a focusing action is not generated in the Y direction. It is more effective to fabricate the aperture in the Y direction greater than the aperture in the X direction. An upper limit is up to a limit on which the aperture can be fabricated.

As illustrated in FIG. 10, in the monochromator MC in accordance with an embodiment of the present invention, in an embodiment of the present invention, the two transfer lenses TL1 and TL2 may be axial symmetric lenses. In this case, the axial symmetric lens may have the same convergence action in the X direction and the Y direction.

Figure 11:
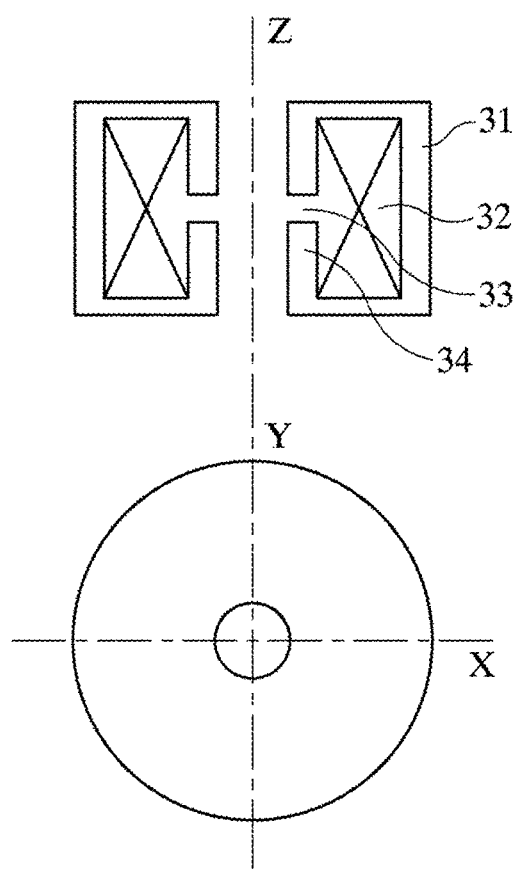
FIG. 11 is a diagram illustrating a magnetic type axial symmetric lens used in a transfer lens in accordance with an embodiment of the present invention.
Figure 12:
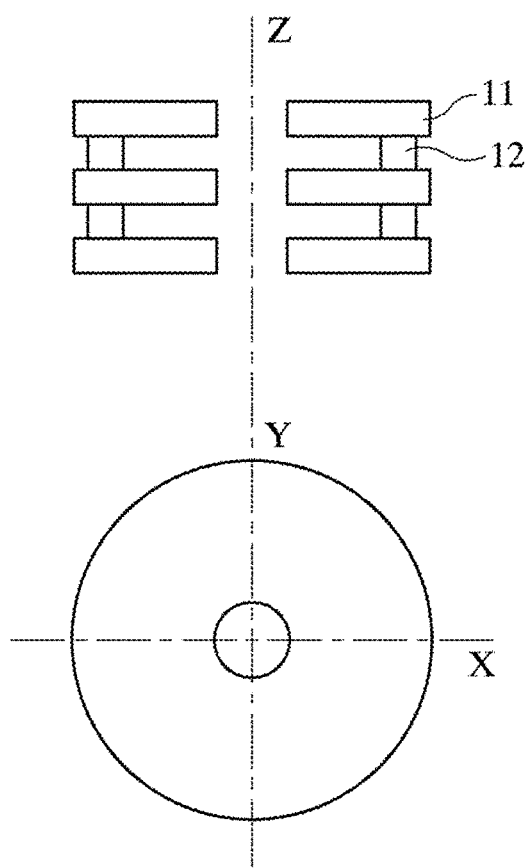
FIG. 12 is a diagram illustrating an electrostatic type axial symmetric lens used in the transfer lens in accordance with an embodiment of the present invention.

In relation to the configuration of the transfer lens, FIG. 11 is a diagram illustrating a magnetic type axial symmetric lens used in the transfer lens in accordance with an embodiment of the present invention, and FIG. 12 is a diagram illustrating an electrostatic type axial symmetric lens used in the transfer lens in accordance with an embodiment of the present invention. As illustrated in FIGS. 11 and 12, the magnetic type axial symmetric lens may include a coil 32, a yoke 31 made of a magnetic substance, and a pole piece 34. The magnetic type axial symmetric lens is a charged particle optical lens configured to produce a magnetic field distribution that is axially symmetrical to the optical axis by a magnetic flux leaked from a gap 33 and to focus the charged particle beam. Furthermore, the electrostatic type axial symmetric lens is a charged particle optical lens configured to include the insulating material 12 between the three electrodes 11 and configured to produce an electric field distribution axially symmetrical to the optical axis and to obtain a focusing action.

The ray of a charged particle beam (i.e., a para-axial ray) Yβ discharged by the emitter at a specific angle β in the Y direction travels in parallel to the axial ray by the first transfer lens TL1. The ray of the charged particle beam (i.e., the para-axial ray) Yβ in the Y direction goes straight without being almost affected by the two-stage cylindrical lens CylL1, CylL2. Thereafter, the para-axial ray Yβ is incident in parallel to the axial ray in the second transfer lens TL2 in the rear and is focused on the axial ray at the location Zi, that is, a focal location behind the second transfer lens TL2 by the axial symmetric lens action of the second transfer lens TL2.

In accordance with the configuration of the optics according to an embodiment of the present invention, a stigmatic image can be obtained in which a charged particle beam is converged on the same location in the X direction and the Y direction. The para-axial ray of the charged particle beam in the Y direction between the location Zo, that is, the location of the emitter, and the location Zi, that is, the location of an image in the rearmost location, is not focused on the axial ray (i.e., 0 times focusing), and has a ray greatly different from the aforementioned para-axial ray that is focused three times in the X direction. In the monochromator MC including the first and the second cylindrical lenses CylL1 and CylL2, that is, the two-stage cylindrical lens, an astigmatic image focused on the axial ray only in the X direction is formed. Accordingly, in accordance with an embodiment of the present invention, it is effective to reduce an electron-electron mutual action (i.e., a Boersh effect, a spatial charge effect) because charged particles are unable to be focused on one point. Furthermore, in accordance with an embodiment of the present invention, there is an advantage in that an aberration in the Y direction is small because a lens action in the Y direction is small.

As illustrated in FIG. 10, in the monochromator MC in accordance with an embodiment of the present invention, in an embodiment of the present invention, the two-stage deflector Deflector2 may be installed at the front and back of the location Ze2, that is, a focal location placed behind the second cylindrical lens CylL2. The para-axial ray Xγ can be accurately matched with the second transfer lens TL2 at the latter part and the axial ray of the optics behind the second transfer lens TL2 by performing shifting and tilting on the para-axial ray Xγ discharged from the cylindrical lens.

Other embodiments of the monochromator MC

Embodiment 1

As illustrated in FIGS. 9 and 10, in the monochromator MC in accordance with another embodiment of the present invention, the two-stage deflector Deflector1 may be installed at the front and back of the location Ze1, that is, a focal location in front of the first cylindrical lens CylL1. The ray of a charged particle beam may be matched with the location where the first cylindrical lens CylL1 placed behind the first transfer lens TL1 is incident by performing shifting and tilting on the para-axial ray Xγ discharged by the emitter through the first transfer lens TL1. For example, there are advantages in that the location of the emitter, such as a rise of the extraction voltage over time, can be changed, the deviation of an axis attributable to a change of a use condition can be finely controlled, and frequency of a change of the offset in the cylindrical lens can be reduced.

Embodiment 2

Figure 13:
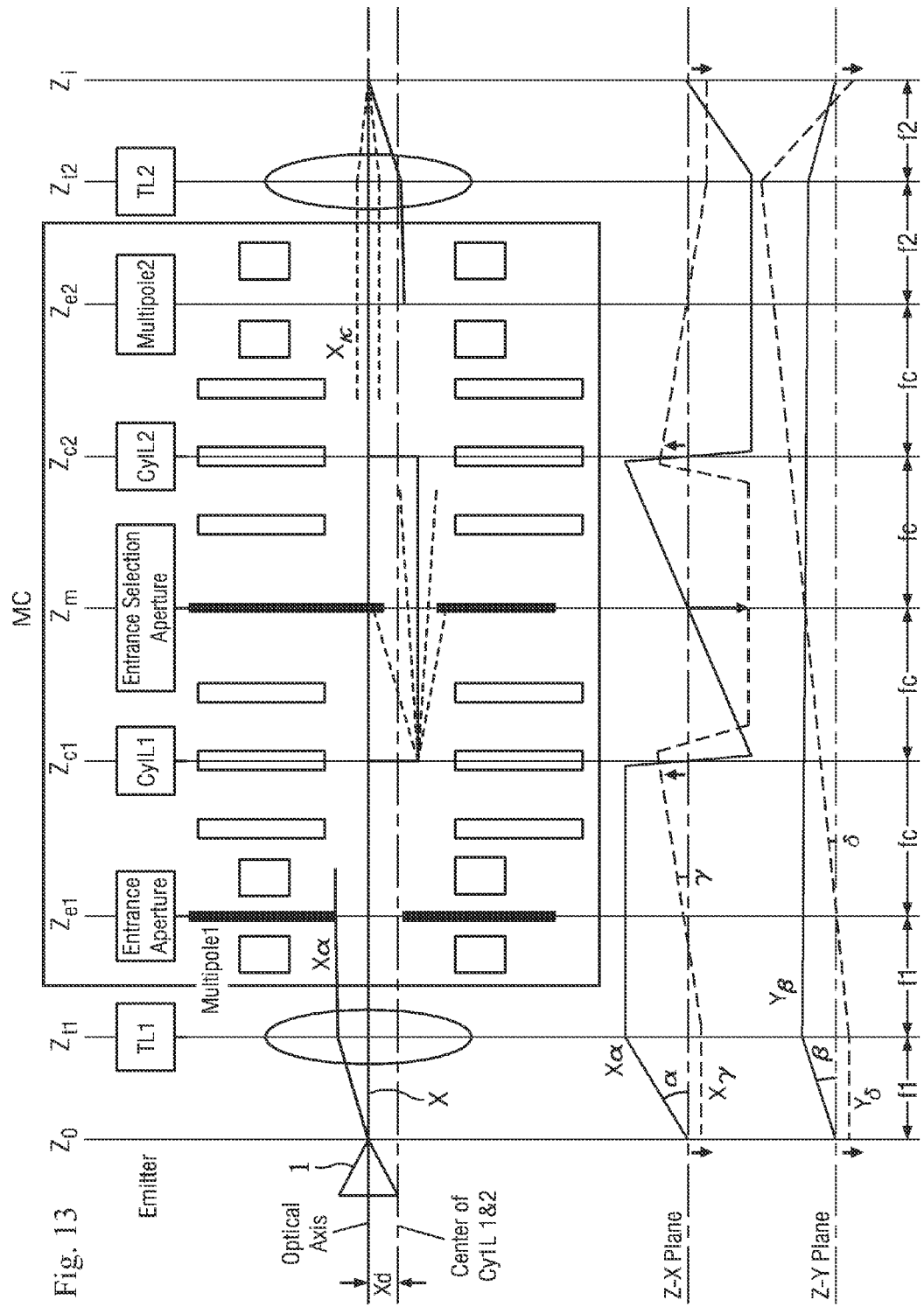
FIG. 13 is a diagram illustrating a monochromator in accordance with another embodiment of the present invention.

In relation to a monochromator MC in accordance with another embodiment of the present invention, FIG. 13 is a diagram illustrating a monochromator in accordance with another embodiment of the present invention. As illustrated in FIG. 13, in another embodiment of the present invention, two multiples formed of electrodes or magnetic poles that are symmetrically split may be disposed in series at the respective locations of a first multipole 1 and a second multipole 2. Electromagnetic fields may be symmetrically applied to the first multipole 1 and the second multipole 2, and a geometric aberration, a chromatic aberration, and a parasitic aberration attributable to a mechanical error may be performed on the first multipole 1 and the second multipole 2. Each of the first and the second multipoles applies a an electromagnetic field that travels symmetrically to the symmetric plane Zm to the charged particle beam, thereby being capable of reducing an influence on the final charged particle beam. The multipoles may be used along with the aforementioned deflectors.

Embodiment 3

Figure 14:
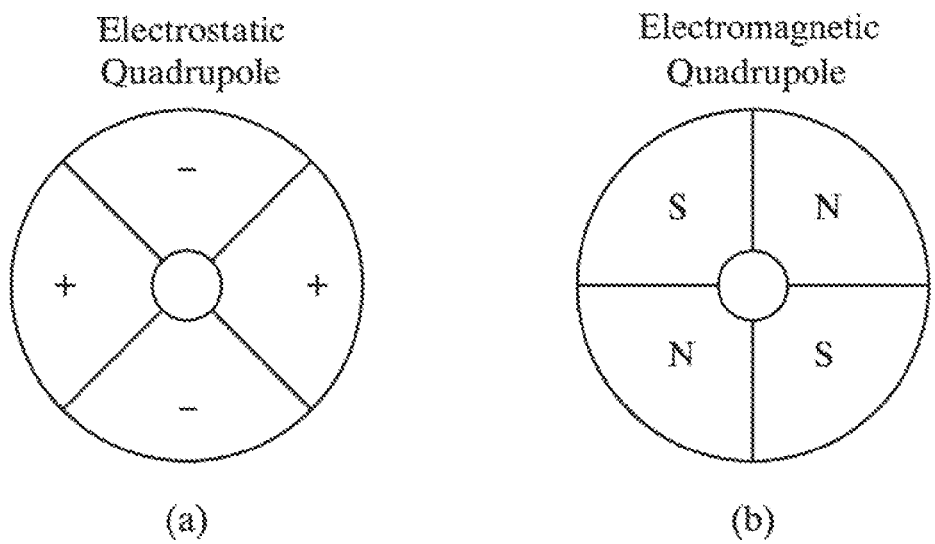

FIG. 13 is a diagram illustrating a monochromator in accordance with another embodiment of the present invention, and FIG. 14 is a diagram illustrating a multipole in accordance with another embodiment of the present invention. As illustrated in FIGS. 13 and 14, in another embodiment of the present invention, two electrodes "a" or magnetic poles "b" each symmetrically divided into four parts may be used in series in each of the locations of the first multipole 1 and the second multipole 2. A multipole in accordance with another embodiment of the present invention may be formed of a quadrupole (or stigmator) which is used in an existing microscope and to which an electromagnetic field is applied so that the electrodes or magnetic poles are subject to two-rotation symmetry (i.e., the same shape is obtained after 180-degree rotation), thus correcting astigmatism occurring in the cylindrical lens, a secondary mix aberration, or a parasitic aberration attributable to mechanical precision. Each quadrupole can reduce an influence on the final charged particle beam by applying a charged particle beam whose electromagnetic field symmetrically travels to the symmetric plane Zm.

Embodiment 4

Figure 15:
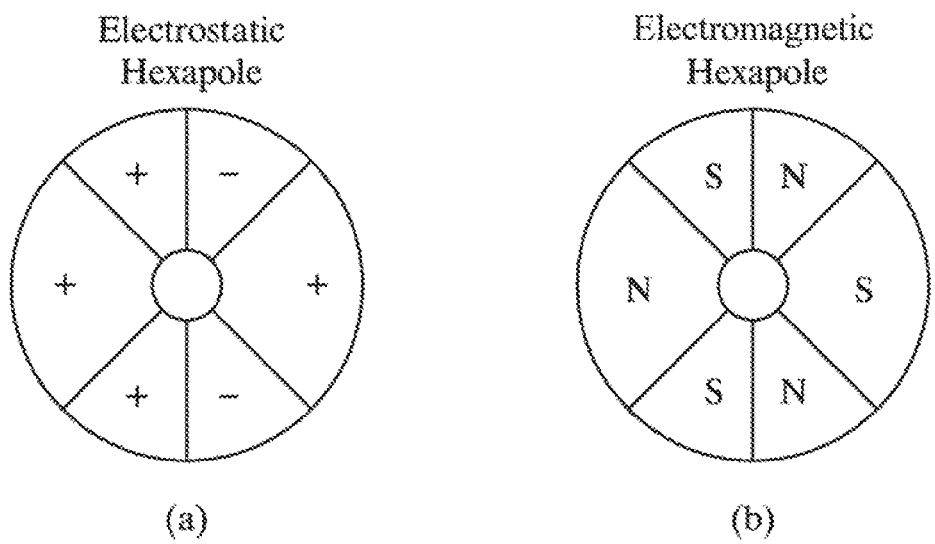

FIG. 15 is a diagram illustrating a multipole in accordance with another embodiment of the present invention. As illustrated in FIGS. 13 and 15, in another embodiment of the present invention, two electrodes or magnetic poles each symmetrically divided into six parts may be disposed in series in the respective locations of the first multipole 1 and the second multipole 2. A multipole in accordance with another embodiment of the present invention may be formed of a hexapole by applying an electric field or magnetic field so that the poles are subject to 3-rotation symmetry (i.e., the same shape is obtained after 120-degree rotation), thus correcting an additional aperture aberration $\alpha 2$ and a primary chromatic aberration $\alpha k$ occurring while passing through the cylindrical lens at the energy selection location Zm. Accordingly, in accordance with another embodiment of the present invention, optics capable of obtaining a high current in the same energy resolution can be realized because the diameter of a charged particle beam is identically maintained in a condition in which a higher current is obtained. Alternatively, energy resolution in the same amount of current can be improved because the diameter of a charged particle beam is reduced in the same current condition. Furthermore, a parasitic aberration attributable to mechanical precision can be corrected. Each hexapole can reduce an influence on the final charged particle beam by applying a charged particle beam whose electromagnetic field symmetrically travels to the symmetric plane Zm.

Embodiment 5

FIG. 16 is a diagram illustrating a multipole in accordance with another embodiment of the present invention. As illustrated in FIGS. 13 and 16, in another embodiment of the present invention, an electrode or magnetic pole symmetrically divided into eight parts may be used in each of the locations of the first multipole 1 and the second multipole 2. A multipole in accordance with another embodiment of the present invention may be formed of an octapole by applying an electric field or magnetic field so that the poles are subject to 4-rotation symmetry (i.e., the same shape is obtained after 90-degree rotation), thus correcting a ternary aperture aberration $\alpha 3$ occurring while passing through the cylindrical lens at the energy selection location Zm. In accordance with another embodiment of the present invention, optics capable of obtaining a high current in the same energy resolution can be realized because the diameter of a charged particle beam is identically maintained in a condition in which a higher current is obtained. Alternatively, energy resolution in the same amount of current can be improved because the diameter of a charged particle beam is reduced in the same current condition. Furthermore, a parasitic aberration attributable to mechanical precision can be corrected. Each octapole can reduce an influence on the final charged particle beam by applying a charged particle beam whose electromagnetic field symmetrically travels to the symmetric plane Zm.

Embodiment 6

In another embodiment of the present invention, two twelve poles each formed of an electrode or magnetic pole symmetrically divided into twelve parts may be disposed in series at each of the locations of the first multipole 1 and the second multipole 2. The twelve poles may be formed by overlapping the aforementioned quadrupole, hexapole, and octapole with each other. In accordance with another embodiment of the present invention, the twelve poles can correct respective aberrations occurring in the cylindrical lens at the energy selection location Zm. In accordance with another embodiment of the present invention, optics capable of obtaining a high current in the same energy resolution can be realized because the diameter of a charged particle beam is identically maintained in a condition in which a higher current is obtained. Alternatively, energy resolution in the same amount of current can be improved because the diameter of a charged particle beam is reduced in the same current condition. Each of the twelve poles can reduce an influence on the final charged particle beam by applying a charged particle beam whose electromagnetic field symmetrically travels to the symmetric plane Zm.

Figure 17:
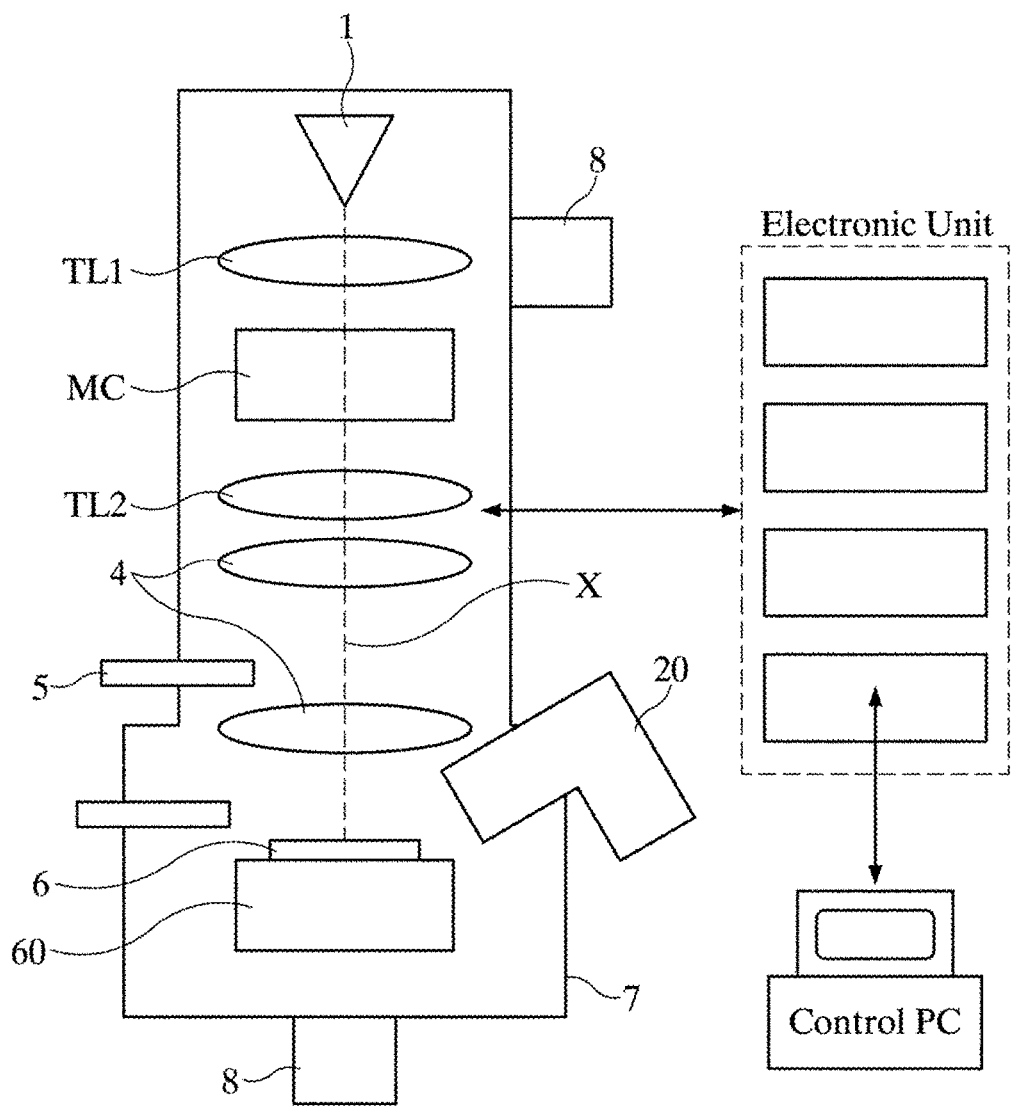
FIGS. 17, 18, and 19 are diagrams illustrating a charged particle beam apparatus in accordance with an embodiment of the present invention.

An example of the configuration of a charged particle beam apparatus including the monochromator MC FIG. 17 is a diagram illustrating the charged particle beam apparatus in accordance with an embodiment of the present invention. As illustrated in FIG. 17, the charged particle beam apparatus in accordance with an embodiment of the present invention may include optics 4, such as a plurality of focusing lenses CL and object lenses OL disposed under the monochromator MC in accordance with an embodiment of the present invention and monitor or process a surface of a sample. The charged particle beam apparatus in accordance with an embodiment of the present invention may include a scanning electron microscope (SEM) using an electron source as an emitter and using an electrostatic or magnetic lens, a focusing ion beam (FIB) apparatus using an ion source (e.g., Ga, in, Au, Bi) as an emitter and using an electrostatic lens, and a helium ion microscope (HIM) using an ion source (e.g., He, Ne, $H_2$, Ar, $O_2$) as an emitter and using an electrostatic lens.

Figure 18:
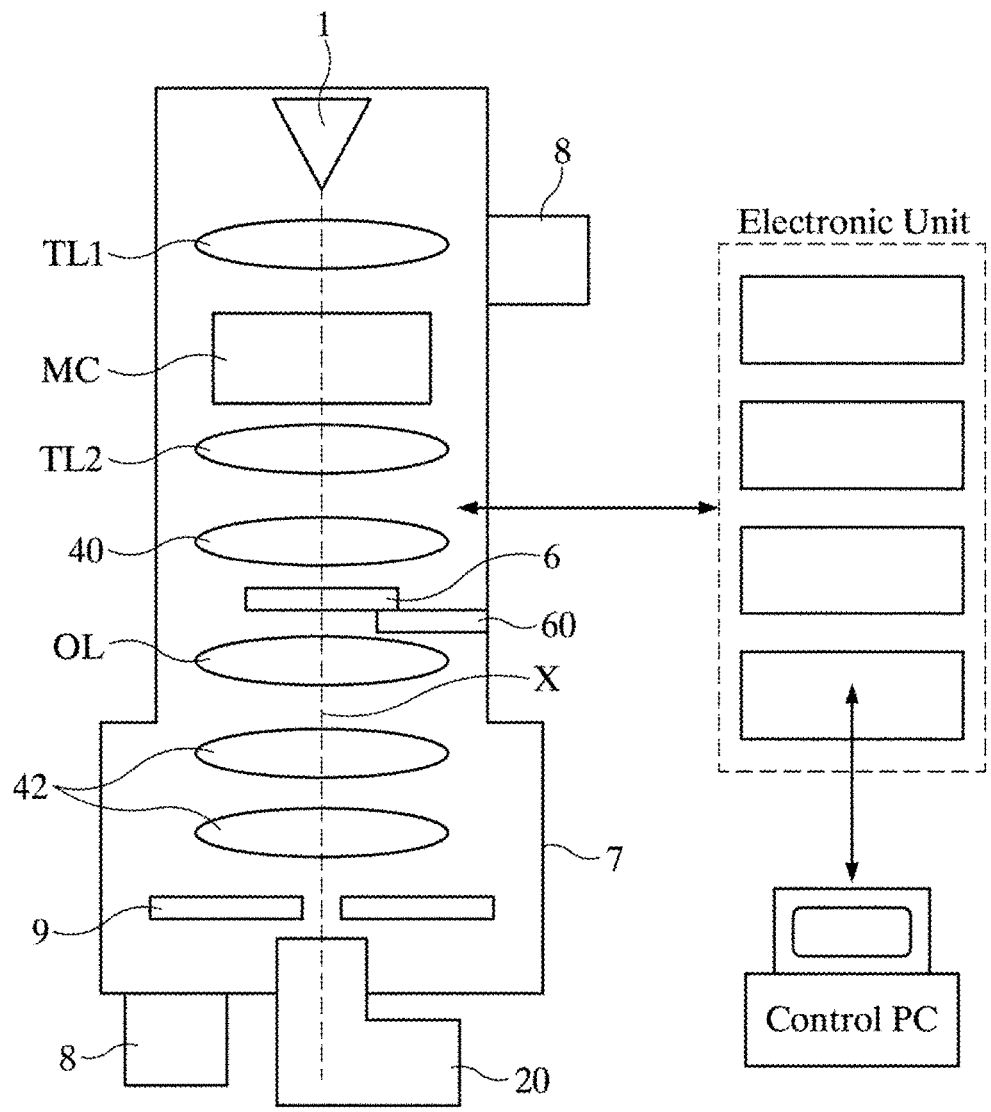

FIG. 18 is a diagram illustrating a charged particle beam apparatus in accordance with an embodiment of the present invention. As illustrated in FIG. 18, the charged particle beam apparatus in accordance with an embodiment of the present invention may include illumination optics 40, an object lens OL, projection optics 42, a screen 9, or a detector 5 disposed under the monochromator MC in accordance with an embodiment of the present invention and monitor or process a sample using transmitted electrons. The charged particle beam apparatus in accordance with an embodiment of the present invention may include a transmission electron microscope (TEM) using an electron source as an emitter and using a magnetic lens or a scanning transmission electron microscope (STEM) using an electron source as an emitter and using a magnetic lens.

Figure 19:
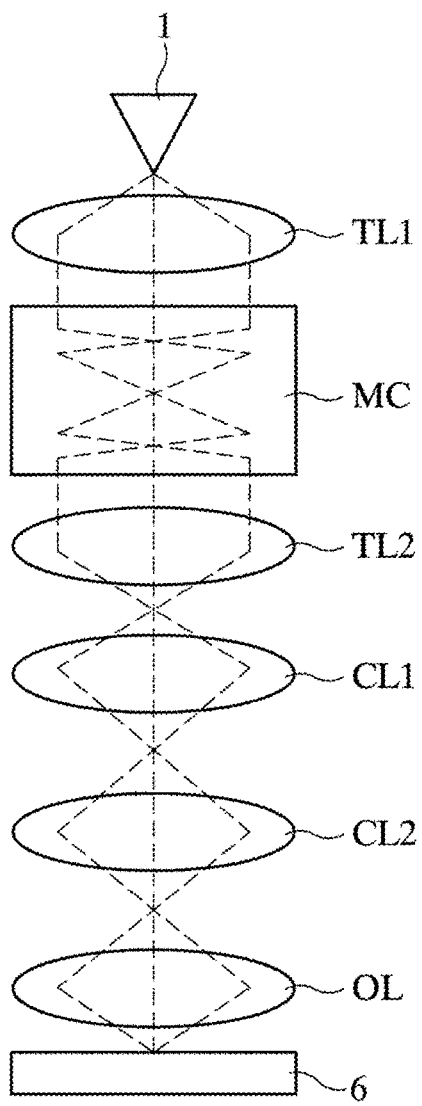

FIG. 19 is a diagram illustrating a charged particle beam apparatus in accordance with an embodiment of the present invention. As illustrated in FIG. 19, the charged particle beam apparatus in accordance with an embodiment of the present invention may include a charged particle beam apparatus for forming a focus formed at the location Zi, that is, the rearmost place of the monochromator MC in accordance with an embodiment of the present invention, the surface of water of an object lens OL through a focusing lens CL on the lower side and focusing a charged particle beam on a sample 6 through the object lens OL. The focusing lens CL may include a plurality of lenses. In accordance with the charged particle beam apparatus according to an embodiment of the present invention, there is an advantage in that an optimal open angle determined by energy of a charged particle beam and the aberration of the optics can be controlled by the focusing lens CL and the object lens OL.

In the charged particle beam apparatus in accordance with an embodiment of the present invention, other elements of the optics are the same as the SEM, FIB, HIM, TEM, and STEM of conventional optics. The charged particle beam in accordance with an embodiment of the present invention may include optical elements, such as various detectors, including a scanner for scanning a charged particle beam, a stigmater for correcting the flying spot of a charged particle beam, an alignment unit for correcting the optical axis of a charged particle beam and the location of a sample, a blanker for blocking a charged particle beam, a secondary electron/reflection electronic detector for a lens, and a secondary electron detector within a sample room. Illumination optics 40 for determining the amount of current for radiating an electron beam to a sample, a radiation angle, and an illumination region and projection optics 42 for enlarging an image of a sample and projecting the image onto a screen 9 may be disposed in a TEM and STEM, such as those illustrated in FIG. 18. A magnification, a view, the switching of a sample image/diffraction image, and a scattering angle can be controlled by the projection optics 42.

A stage 60 for changing the locations X, Y, and Z and angle (rotation, tilt) of a sample with respect to a charged particle beam and the transfer system of a sample may also be included in the charged particle beam apparatus. Furthermore, a charged particle beam is surrounded by a metal vacuum chamber 7 because charged particles require a vacuum environment. The vacuum chamber 7 may include one or more vacuum pumps 8. In general, a plurality of ion pumps for obtaining good vacuum may be disposed in a turbo pump, an electron gun chamber, and a middle chamber within the sample room. Furthermore, a gate valve for dividing the electron gun chamber and the sample room and a load rock chamber for replacing a sample may also be installed.

The charged particle optical apparatus that adopts the configuration of the monochromator MC in accordance with an embodiment of the present invention is advantageous in that the contribution of a chromatic aberration is reduced and resolution is improved because an emitter has narrow energy diffusion.

The charged particle beam apparatus configured to include the monochromator MC in accordance with an embodiment of the present invention and to monitor a surface of a sample may have the function of an electron energy loss spectroscopy (EELS) 20 for analyzing energy of secondary electrons emitted from a surface of a sample. The charged particle beam apparatus according to an embodiment of the present invention may analyze a local composition, chemical combination state, electron state, dielectric function, and phonon state of a sample.

The charged particle beam apparatus configured to include the monochromator MC in accordance with an embodiment of the present invention and to monitor a sample using transmitted electrons may have the function of the electron energy loss spectroscopy (EELS) 20 for performing spectroscopy on energy of a transmitted electron beam. The charged particle beam apparatus according to an embodiment of the present invention may analyze a local composition, chemical combination state, electron state, dielectric function, and phonon state of a sample. If both the aforementioned charged particle beam apparatuses in accordance with embodiments of the present invention include the electron energy loss spectroscopy (EELS) 20, the improvement of energy resolution may be expected because a primary charged particle beam has small energy diffusion.

Another Embodiment 1

Figure 20:
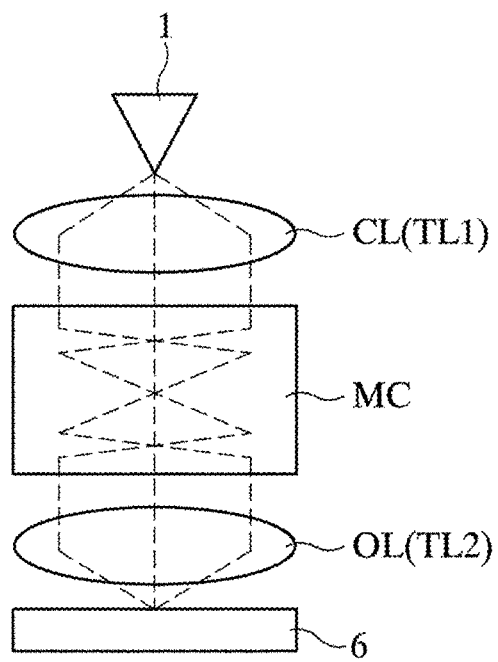
FIGS. 20, 21, 22, 23, and 24 are diagrams illustrating a charged particle beam apparatus in accordance with another embodiment of the present invention.

FIG. 20 is a diagram illustrating a charged particle beam apparatus in accordance with another embodiment of the present invention. As illustrated in FIG. 20, optics in which the first transfer lens TL1 and second transfer lens TL2 of the monochromator MC in accordance with an embodiment of the present invention are used as a focusing lens and an object lens are effective in an SEM and FIB that are particularly used in a low acceleration voltage. In accordance with another embodiment 1 of the present invention, the influence of a spatial charge effect can be reduced because optics not having a focus point in a column can be realized. Furthermore, in accordance with another embodiment 1 of the present invention, stiffness can be increased and anti-vibration can be improved because the number of optical elements is reduced and the length of equipment is made small. In this case, the size of the emitter is reduced so that a ratio of the focal distances of the first transfer lens TL1 and the second transfer lens TL2 becomes $f2/f1=0.05\sim0.3$.

Another Embodiment 2

Figure 21:
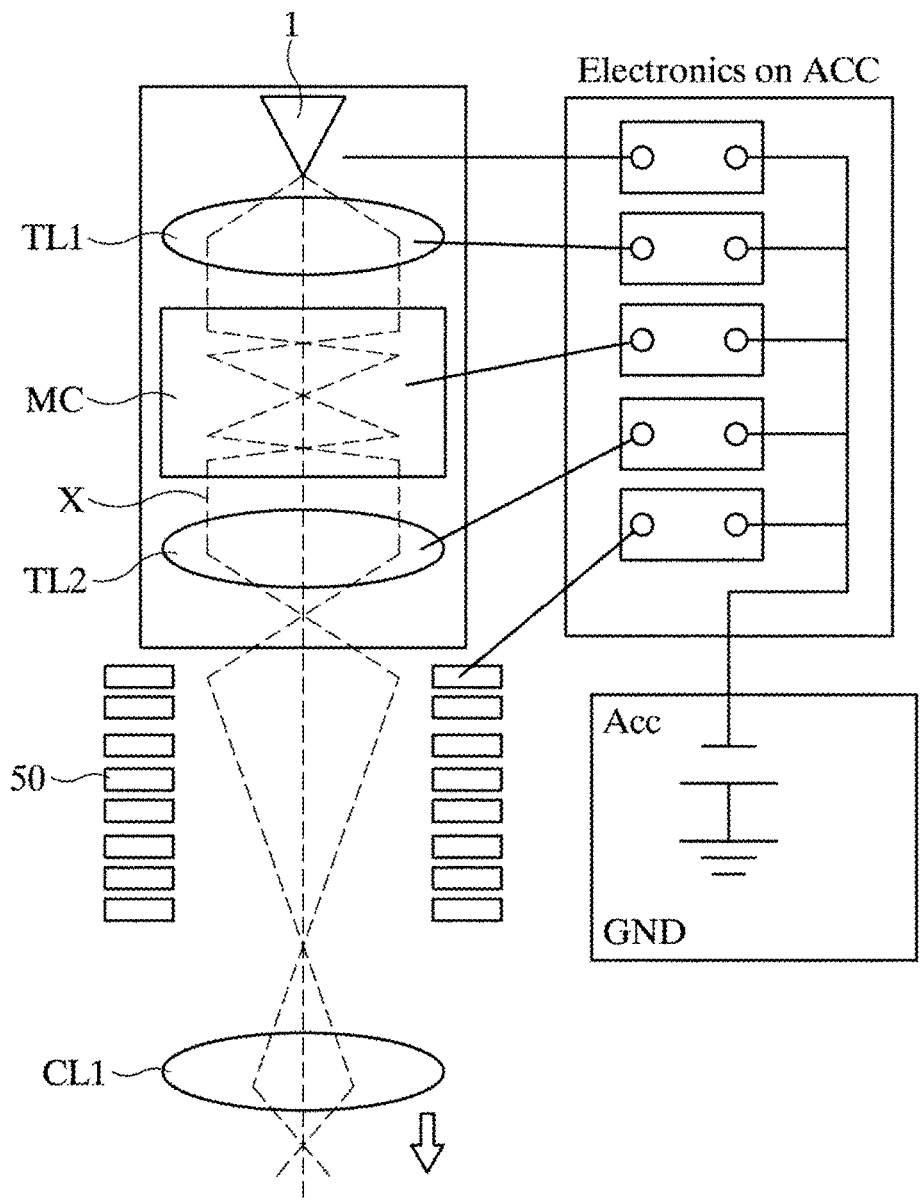

FIG. 21 is a diagram illustrating a charged particle beam apparatus in accordance with another embodiment of the present invention. As illustrated in FIG. 21, if the monochromator MC in accordance with an embodiment of the present invention is integrated with the high voltage part of an electron gun, in particular, it is effective in a charged particle beam apparatus, such as a transmission electron microscope (TEM) and a scanning transmission electron microscope (STEM) having high charged particle beam energy. An acceleration tube 50 may be disposed behind the location Zi and used as a TEM or STEM of 60~300 keV. In this case, energy of charged particles generated by the monochromator MC is about 3-5 keV determined at the extraction voltage of the emitter, and an acceleration voltage applied by the acceleration tube 50 in the rear stage is accelerated with 100~300 keV. Energy resolution in the monochromator MC is constant because energy of the monochromator MC is almost constant. It is necessary to provide the deflection voltage of the deflector Deflector2 and a piezo power source for finely controlling the aperture, together with the center electrode voltages of the first and the second cylindrical lenses CylL1 and CylL2, to the acceleration voltage in an overlapping way.

Another Embodiment 3

Figure 22:
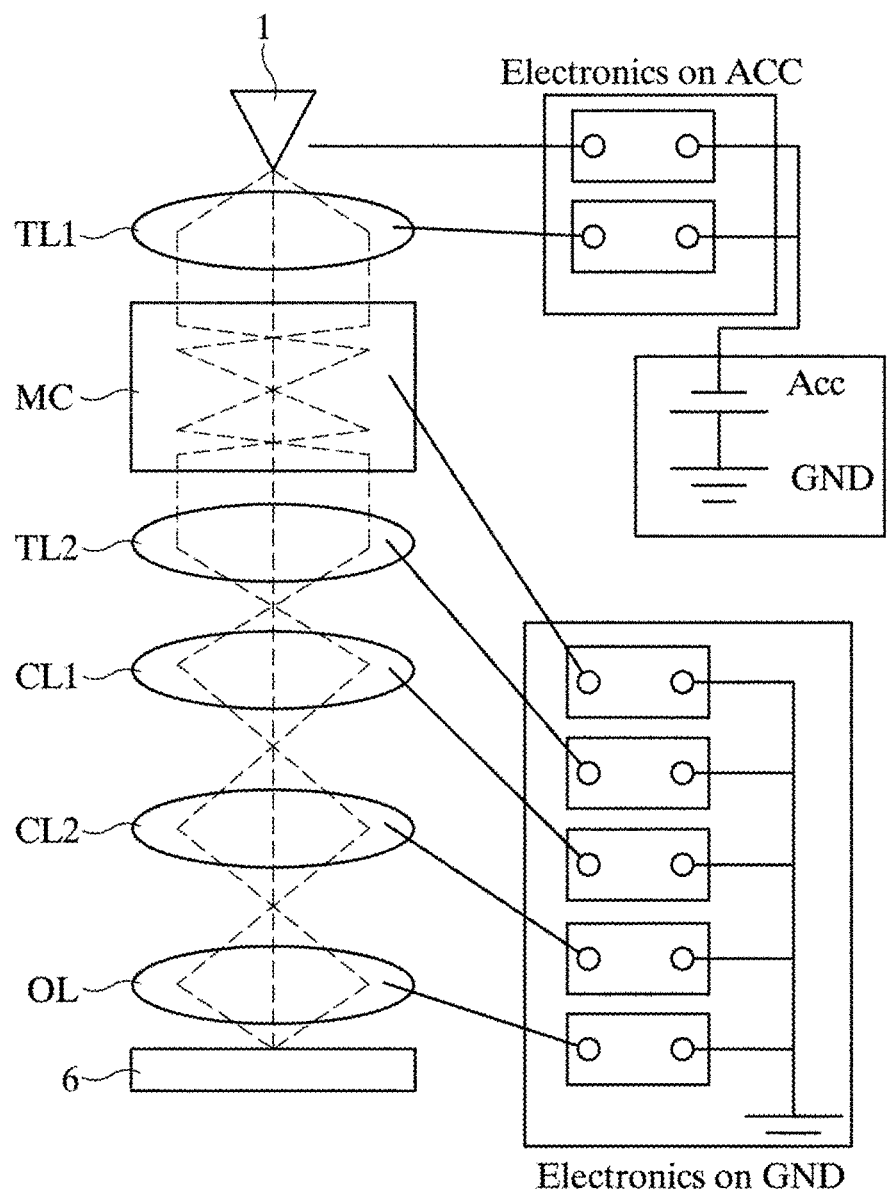

FIG. 22 is a diagram illustrating a charged particle beam apparatus in accordance with another embodiment of the present invention. As illustrated in FIG. 22, the charged particle beam apparatus in which the monochromator MC in accordance with an embodiment of the present invention is used based on the ground may be provided. If the interval between the electrodes of the two-stage cylindrical lens CylL1, CylL2 is 10 mm, a voltage of about 60 kV may be applied to the center electrode, and an acceleration voltage of up to 60 keV may be used. However, performance of the monochromator MC can be improved in low acceleration and a charged particle beam having a narrow energy width can be obtained because energy resolution in the monochromator MC is in inverse proportion to the acceleration voltage. There is an advantage in that the fabrication of an electrical system is facilitated because the deflection voltage of the deflector Deflector2 and the piezo power source for finely controlling the aperture become ground bases. Higher stability of power and a low noise are required because the center electrode voltage of the two-stage cylindrical lens CylL1, CylL2 needs to have high-voltage output.

Another Embodiment 4

Figure 23:
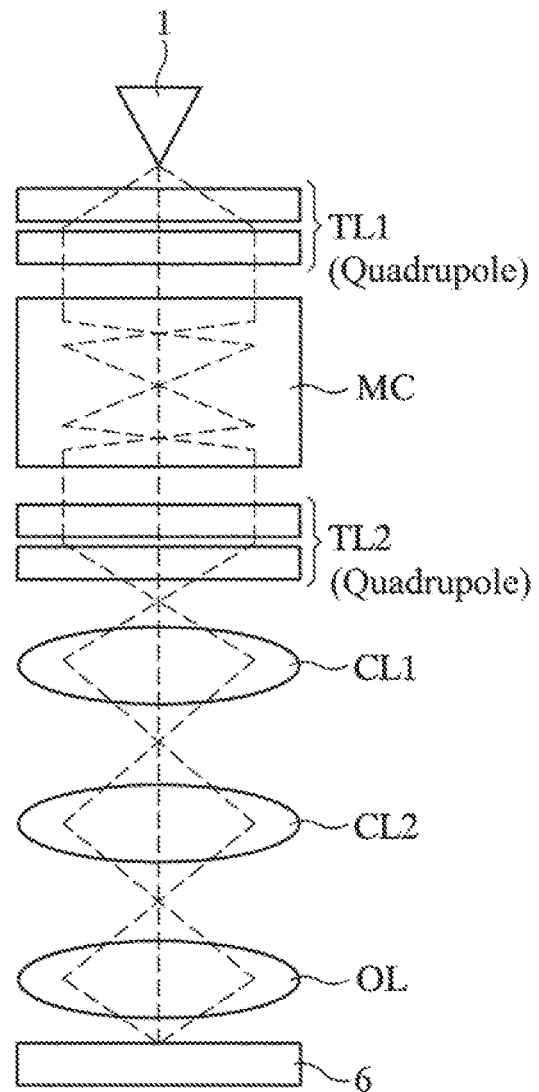
Figure 24:
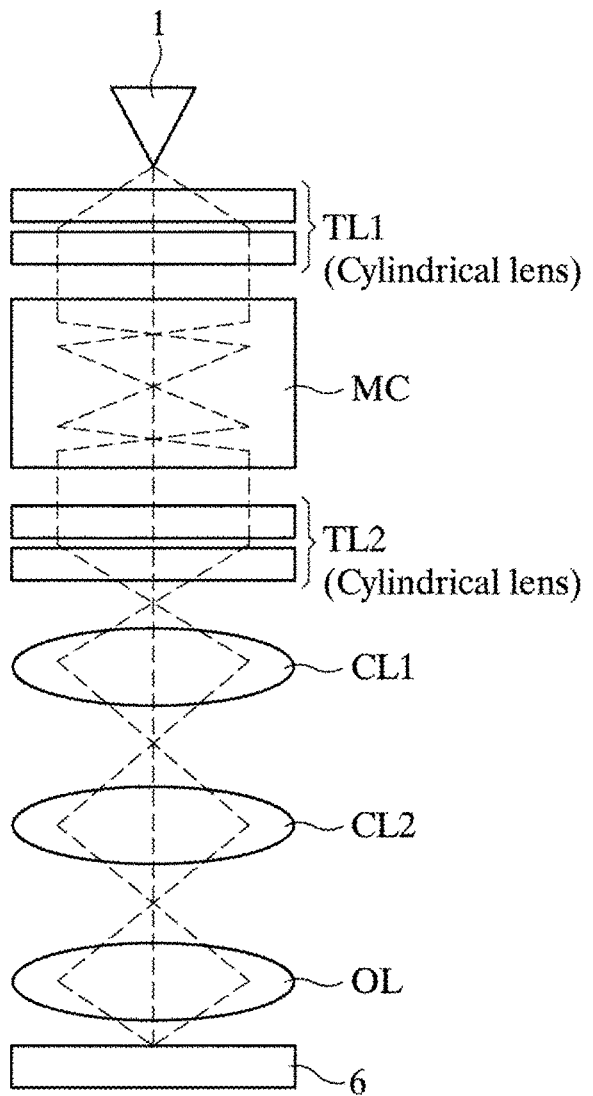

FIG. 23 is a diagram illustrating a charged particle beam apparatus in accordance with another embodiment of the present invention. As illustrated in FIG. 23, in another embodiment of the present invention, a two-stage quadrupole may be used in each of a first transfer lens TL1 and a second transfer lens TL2. The quadrupole has a quartered structure, such as that illustrated in FIG. 14, and has an action for focusing a charged particle beam in one direction and emitting the charged particle beam in the other direction. If such quadrupoles are disposed in two stages in the Z direction, focusing is possible in the X and Y directions, and X and Y focal distances can be independently set (f1$x$, f1$y$, f2$x$, f2$y$). Accordingly, there is an advantage in that a difference between X and Y focal distances attributable to a slight focusing action of the cylindrical lens in the Y direction can be corrected. Furthermore, in order to increase the degree of freedom in setting, a three-stage quadrupole may be used in each of the first transfer lens TL1 and the second transfer lens TL2.

Another Embodiment 5

FIG. 23 is a diagram illustrating a charged particle beam apparatus in accordance with another embodiment of the present invention. As illustrated in FIG. 23, in another embodiment of the present invention, a two-stage cylindrical lens may be used in each of a first transfer lens TL1 and a second transfer lens TL2. The cylindrical lens is configured to have a convergence action in one direction as illustrated in FIG. 1. The charged particle beam apparatus can have convergence actions in two X and Y directions because the two-stage cylindrical lenses are disposed in the first transfer lens TL1 and the second transfer lens TL2, and X and Y focal distances can be independently set (f1$x$, f1$y$, f2$x$, f2$y$). Accordingly, there is an advantage in that a difference between X and Y focal distances attributable to a slight focusing action of the cylindrical lens in the Y direction can be corrected.

APPLICATION EXAMPLE

The configuration of the monochromator MC in accordance with an embodiment of the present invention is effective in a scanning electron microscope (SEM). In particular, performance is expected to be greatly improved using the monochromator MC in accordance with an embodiment of the present invention because a CD-SEM and a DR-SEM used in the management of semiconductor processes are chiefly used in low acceleration and greatly influenced by a chromatic aberration. Furthermore, a conventional SEM has a disadvantage in that the time is taken to adjust an optical axis in order for the SEM to be used in almost constant conditions (e.g., an acceleration voltage and an electric current). However, there is an advantage in that such a disadvantage is reduced using the monochromator MC in accordance with an embodiment of the present invention.

The configuration of the monochromator MC in accordance with an embodiment of the present invention is effective in a focusing ion beam (FIB) apparatus. The contribution of a chromatic aberration is reduced if the monochromator MC in accordance with an embodiment of the present invention is mounted on the charged particle beam apparatus because an ion source has an energy width of 5 keV or more. Accordingly, performance in a middle current region and a low energy region is expected to be improved. Furthermore, unlike in the Wien filter, the monochromator MC according to an embodiment of the present invention adopts an electrostatic type using an electric field, and is more effective because there is no separation using an isotope of ions. For the same reason, the monochromator MC according to an embodiment of the present invention is effective in a helium ion microscope (HIM) using a gas ion as an emitter.

The configuration of the monochromator MC in accordance with an embodiment of the present invention is effective in a transmission electron microscope (TEM) and a scanning transmission electron microscope (STEM) used in a low acceleration region. Since the TEM and the STEM are greatly influenced by a chromatic aberration, performance is expected to be significantly improved using the monochromator MC in accordance with an embodiment of the present invention.

The configuration of the monochromator MC in accordance with an embodiment of the present invention is effective even in a charged particle beam apparatus in which an SEM has an electron energy loss spectroscope (EELS) function because a primary electron beam has small energy diffusion and thus energy resolution is expected to be improved. Furthermore, the monochromator MC in accordance with an embodiment of the present invention may also be applied to an SEM-EELS apparatus capable of spectroscopy for the phonons of gas molecules absorbed by a surface of a sample.

The configuration of the monochromator MC in accordance with an embodiment of the present invention is effective even in a charged particle beam apparatus in which a TEM, an STEM has an electron energy loss spectroscope (EELS) function because a primary electron beam has small energy diffusion and thus energy resolution is expected to be improved. Furthermore, the monochromator MC in accordance with an embodiment of the present invention may also be applied to an (S)TEM-EELS apparatus capable of spectroscopy for the phonons of gas molecules absorbed by a surface of a sample.

The monochromator MC in accordance with an embodiment of the present invention may have a problem in that an electron-electron mutual action is increased in a low energy region for deceleration compared to a Wien filter electrostatic deflector, but can reduce the electron-electron mutual action because an electric current in the monochromator MC is reduced by limiting an electric current using the aperture before a charged particle beam is incident on the monochromator MC.

As described above, an embodiment of the present invention has the following advantages.

First, in accordance with an embodiment of the present invention, there is an advantage in that a charged particle beam having an excellent profile even after passing through the monochromator can be obtained. In other words, there is an advantage in that a charged particle beam at the central part of an emitter can be used.

Second, in accordance with an embodiment of the present invention, there is an advantage in that smaller energy spread (e.g., 10 meV) even after a charged particle beam passes through the monochromator can be realized.

Third, in accordance with an embodiment of the present invention, there is an advantage in that the electric current of a charged particle beam can be further stabilized because a charged particle beam at the central part of an emitter can be used.

Fourth, in accordance with an embodiment of the present invention, there are advantages in that the columns of optics having a straight structure can maintain a cylindrical shape and high mechanical strength and coaxial precision can be obtained. Furthermore, there is an advantage in that the monochromator MC can be used as common optics by turning off the voltage of the cylindrical lens CyL if the monochromator MC does not need to be used in such a way as to use a high current.

Fifth, in accordance with an embodiment of the present invention, there is an advantage in that a charged particle beam can also be used as an ion beam because the entire monochromator MC adopts an electrostatic method. In accordance with an embodiment of the present invention, there are advantages in that the degree of vacuum can be easily improved because there is no gas emitted from the coils and the monochromator MC can be used near an electron gun that requires ultra-high vacuum and extreme high vacuum. Furthermore, there is an advantage in that responsiveness is excellent because there is no hysteresis and the monochromator MC can rapidly switch to On/OFF.

Sixth, in accordance with an embodiment of the present invention, there is an advantage in that a mechanical structure and the configurations of electrical and control systems are simplified because the multipole is used as a lens. Accordingly, excellent efficiency can be achieved with a low cost compared to the aforementioned conventional another monochromators MC.

Seventh, in accordance with an embodiment of the present invention, there is an advantage in that the formation of an astigmatic image in the monochromator MC (e.g., three times in the X direction and 0 times in the Y direction) can be reduced without an increase in the energy spread of an electron-electron mutual action and an increase in the diameter of a charged particle beam.

Those skilled in the art to which the present invention pertains will understand that the present invention may be implemented in other detailed forms without changing the technical spirit or indispensable characteristics of the present invention. Accordingly, it will be understood that the aforementioned embodiments are illustrative and not limitative from all aspects. The scope of the present invention is defined by the appended claims rather than the detailed description, and the present invention should be construed as covering all modifications or variations derived from the meaning and scope of the appended claims and their equivalents.

What is claimed is:

1. A monochromator, comprising:
a first electrostatic lens configured to have a charged particle beam discharged by an emitter incident on the first electrostatic lens, refract a ray of the charged particle beam, and comprise a plurality of electrodes; and
a second electrostatic lens spaced apart from the first electrostatic lens at a specific interval and configured to have a central axis disposed identically with a central axis of the first electrostatic lens, have the charged particle beam output by the first electrostatic lens incident on the second electrostatic lens, refract the ray of the charged particle beam, and comprise a plurality of electrodes,
wherein the charged particle beam is configured to pass through an off-axis ray deviated from the central axis by a specific offset, and when the charged particle beam passes through the electrostatic lenses, an energy width of the charged particle beam is reduced.

2. The monochromator of claim 1, wherein:
the off-axis ray of the charged particle beam is incident on the first electrostatic lens in parallel to the central axis,
the first electrostatic lens is configured to refract the incident off-axis ray of the charged particle beam in a direction opposite a direction in which the off-axis ray of the charged particle beam is incident based on the central axis and output the refracted off-axis ray,
the off-axis ray of the charged particle beam output by the first electrostatic lens is incident on the second electrostatic lens in parallel to the central axis, and
the second electrostatic lens is configured to refract the incident off-axis ray of the charged particle beam in a direction opposite a direction in which the off-axis ray of the charged particle beam is incident on the second electrostatic lens based on the central axis.

3. The monochromator of claim 1, further comprising:
a first slit disposed between the first electrostatic lens and the second electrostatic lens and configured to remove a component having a specific energy range from the charged particle beam; and
a second slit disposed at a location corresponding to a distance that is ½ of the specific interval in front of the first electrostatic lens and configured to limit an incident angle of the charged particle beam.

4. The monochromator of claim 1, wherein:
each of the first and the second electrostatic lenses comprises three electrodes,
a high voltage applied to a center electrode of the three electrodes and a ground voltage is applied to the electrodes on both sides,
each of the three electrodes comprises a rectangular opening at its central part,
the rectangular openings have an identical center,
the openings of the respective electrodes have an identical short-side directions, and
the centers of the openings form an axis identical with the central axes of the first and the second electrostatic lenses.

5. The monochromator of claim 4, wherein:
remaining conditions are calculated based on at least one of conditions comprising the voltage applied to the center electrode, an amount of the offset, and the ½ size of the specific interval, and
the calculated remaining condition are incorporated.

6. The monochromator of claim 1, further comprising:
a first slit disposed between the first electrostatic lens and the second electrostatic lens and configured to remove a component having a specific energy range from the charged particle beam; and
a second slit disposed at a location corresponding to a distance that is ½ of the specific interval in front of the first electrostatic lens and configured to limit an incident angle of the charged particle beam,
wherein each of electrodes forming each of the first and the second electrostatic lenses comprises a rectangular opening in its central part,
the rectangular openings have an identical center,
the openings of the respective electrodes have identical short-side directions,
the centers of the openings form an axis identical with the central axes of the first and the second electrostatic lenses,
in a charged particle beam which travels on a first plane comprising a short-side direction and off-axis ray direction of the openings,
a first charged particle beam incident in parallel to the off-axis ray in the second slit is focused on 에시 the off-axis ray in the first slit after passing through the first electrostatic lens,
a second charged particle beam incident at a specific angle to the off-axis ray in the second slit travels in parallel to the off-axis ray in the first slit after passing through the first electrostatic lens and is focused on the off-axis ray at the location of the distance that is ½ of the specific interval in a rear of the second electrostatic lens after passing through the second electrostatic lens.

7. The monochromator of claim 6, further comprising:
a first axial symmetric lens disposed in front of the monochromator so that a post focal location is identical with a location of the second slit; and
a second axial symmetric lens disposed so that a pre-focal location is identical with the location of the distance that is ½ of the specific interval in the rear of the second electrostatic lens and an image of the emitter is formed at the post focal location,
wherein the emitter is disposed at the pre-focal location of the first axial symmetric lens.

8. The monochromator of claim 6, wherein:
a long side of the openings of the first and the second electrostatic lenses is ten times or more of a short side of the openings of the first and the second electrostatic lenses,
a focusing action for the charged particle beam is present in the short-side direction,
a focusing action for the charged particle beam is not present in the long side direction, and
the charged particle beam is not focused in the rear of the second electrostatic lens in the emitter.

9. The monochromator of claim 6, further comprising:
a first two-stage deflector provided at the location of the distance that is ½ of the specific interval in the rear of the second electrostatic lens; and
a second two-stage deflector provided based on the location of the second slit.

10. The monochromator of claim 9, wherein each of the first and the second two-stage deflector comprises a quadrupole, hexapole, or twelve pole.

11. The monochromator of claim 1, wherein:
fc that is a second focal distance between the first electrostatic lens and the second electrostatic lens is defined as a distance from a location where the ray of the charged particle beam incident in parallel to the off-axis ray is converged secondly in the off-axis ray to a center of the electrostatic lens, and
a distance between the first electrostatic lens and the second electrostatic lens is 2fc.

12. A charged particle beam apparatus, comprising:
an emitter configured to discharge a charged particle beam;
a monochromator configured to have the charged particle beam pass through the monochromator and has a function for reducing an energy width of the charged particle beam according to claim 1;
a sample configured to have the charged particle beam radiated on the sample;
a stage configured to maintain and move the sample;
a detector configured to detect a secondary particle beam generated from the charged particle beam in the sample;
an electrical system configured to drive functions of the emitter, the optics, the stage and the detector; and
a control system configured to control the electrical system.

13. The charged particle beam apparatus of claim 12, further comprising at least one axial symmetric lens disposed in a rear of the monochromator, wherein a surface of the sample is monitored or processed by scanning the charged particle beam on the sample.

14. The charged particle beam apparatus of claim 13, further comprising an electron energy loss spectroscopy (EELS) configured to have an EELS function for performing spectroscopy on energy of the secondary particle beam emitted from a surface of the sample.

15. The charged particle beam apparatus of claim 12, further comprising:
at least one axial symmetric lens disposed in at least one of a back of the monochromator, a front of the sample, and back of the sample; and
a screen configured to have the charged particle beam projected on the screen; and
the detector configured to detect the projected charged particle beam,
wherein the sample is monitored using charged particles detected after the screen transmit the charged particles.

16. The charged particle beam apparatus of claim 15, further comprising an electron energy loss spectroscopy (EELS) configured to have an EELS function for performing spectroscopy on energy of the secondary particle beam emitted from a surface of the sample.

17. The charged particle beam apparatus of claim 12, further comprising:
a second axial symmetric lens provided in a rear of the monochromator, configured to have a pre-focal location identical with a location of a distance that is ½ of a specific interval of the monochromator in a rear of a second electrostatic lens which is one element of the monochromator, and disposed so that an image of the emitter is formed at a post focal location; and
a plurality of third axial symmetric lenses disposed in a rear of the second axial symmetric lens,
wherein the image of the emitter formed at the post focal location of the second axial symmetric lens is reduced by a third axial symmetric lens and formed in the sample.

18. The charged particle beam apparatus of claim 12, further comprising:
a second axial symmetric lens provided in a rear of the monochromator, configured to have a pre-focal location identical with a location of a distance that is ½ of a specific interval of the monochromator in a rear of a second electrostatic lens which is one element of the monochromator, and disposed so that an image of the emitter is formed at a post focal location; and a plurality of third axial symmetric lenses disposed in a rear of the second axial symmetric lens, wherein the second axial symmetric lens focuses the charged particle beam on the sample.

19. The charged particle beam apparatus of claim 12, further comprising:

a quadrupole lens for X-direction focusing and a quadrupole lens for Y-direction focusing provided in series in front of the monochromator and disposed so that a pre-focal location is identical with a location of the emitter and a post focal location is identical with a location of a second slit which is one element of the monochromator; and a quadrupole lens for X-direction focusing and a quadrupole lens for Y-direction focusing provided in series in a rear of the monochromator and disposed so that a pre-focal location is identical with a location of a distance that is ½ of a specific interval of the monochromator in a rear of the second electrostatic lens which is one element of the monochromator and an image of the emitter is formed at a post focal location.

20. The charged particle beam apparatus of claim 12, further comprising:

a cylindrical lens for X-direction focusing and a cylindrical lens for Y-direction focusing provided in series in front of the monochromator and disposed so that a pre-focal location is identical with a location of the emitter and a post focal location is identical with a location of a second slit which is one element of the monochromator; and a cylindrical lens for X-direction focusing and a cylindrical lens for Y-direction focusing provided in series in a rear of the monochromator and disposed so that a pre-focal location is identical with a location of a distance that is ½ of a specific interval of the monochromator in a rear of the second electrostatic lens which is one element of the monochromator and an image of the emitter is formed at a post focal location.

* * * * *